US012152228B2

(12) United States Patent
Haneda et al.

(10) Patent No.: US 12,152,228 B2
(45) Date of Patent: *Nov. 26, 2024

(54) SCAFFOLDING MATERIAL FOR CELL CULTURES AND CELL CULTURE METHOD USING SAME

(71) Applicant: SEKISUI CHEMICAL CO., LTD., Osaka (JP)

(72) Inventors: Satoshi Haneda, Osaka (JP); Yuriko Manabe, Osaka (JP); Ryoma Ishii, Osaka (JP); Hiroki Iguchi, Osaka (JP); Hiroshi Yamauchi, Osaka (JP); Takahiro Omura, Saitama (JP)

(73) Assignee: SEKISUI CHEMICAL CO., LTD., Osaka (JP)

(*) Notice: Subject to any disclaimer, the term of this patent is extended or adjusted under 35 U.S.C. 154(b) by 909 days.

This patent is subject to a terminal disclaimer.

(21) Appl. No.: 16/919,312

(22) Filed: Jul. 2, 2020

(65) Prior Publication Data
US 2020/0407672 A1    Dec. 31, 2020

Related U.S. Application Data

(63) Continuation-in-part of application No. 16/958,204, filed as application No. PCT/JP2018/048386 on Dec. 27, 2018.

(30) Foreign Application Priority Data

Dec. 27, 2017  (JP) ................................. 2017-252420

(51) Int. Cl.
*C12M 1/12*   (2006.01)
*C12N 5/071*  (2010.01)
*C12N 5/074*  (2010.01)

(52) U.S. Cl.
CPC ............. *C12M 25/14* (2013.01); *C12N 5/067* (2013.01); *C12N 5/0696* (2013.01); *C12N 2533/30* (2013.01); *C12N 2539/00* (2013.01)

(58) Field of Classification Search
CPC ...... C12M 25/14; C12N 5/067; C12N 5/0696; C12N 2533/30; C12N 2539/00
USPC .......................................................... 435/370
See application file for complete search history.

(56) References Cited

U.S. PATENT DOCUMENTS

| | | | |
|---|---|---|---|
| 4,537,790 | A | 8/1985 | Horodniceanu et al. |
| 5,393,668 | A | 2/1995 | Cinatl et al. |
| 5,880,216 | A | 3/1999 | Tanihara et al. |
| 6,984,692 | B2 | 1/2006 | Kumaki et al. |
| 8,153,715 | B2 | 4/2012 | Stark |
| 2002/0161440 | A1 | 10/2002 | Son et al. |
| 2005/0164377 | A1 | 7/2005 | Miyabayashi et al. |
| 2006/0235084 | A1 | 10/2006 | Heller et al. |
| 2007/0122901 | A1 | 5/2007 | Morita et al. |
| 2009/0130756 | A1 | 5/2009 | Klann et al. |
| 2009/0176937 | A1 | 7/2009 | Frank et al. |
| 2011/0129924 | A1 | 6/2011 | Ying et al. |
| 2011/0318829 | A1 | 12/2011 | Tazaki et al. |
| 2012/0015177 | A1* | 1/2012 | Kim ..................... B32B 27/365 264/319 |
| 2012/0202070 | A1 | 8/2012 | Asanuma et al. |
| 2013/0280725 | A1 | 10/2013 | Ismagilov et al. |
| 2013/0309679 | A1 | 11/2013 | Ismagilov et al. |
| 2014/0210338 | A1 | 7/2014 | Matsumura et al. |
| 2014/0315235 | A1 | 10/2014 | Puschmann et al. |
| 2015/0010919 | A1 | 1/2015 | Feinberg et al. |
| 2015/0140652 | A1 | 5/2015 | Sasai et al. |
| 2018/0126713 | A1 | 5/2018 | Glaser et al. |
| 2018/0194935 | A1 | 7/2018 | Maeda et al. |
| 2019/0106561 | A1 | 4/2019 | Ukidwe |
| 2020/0362289 | A1 | 11/2020 | Haneda et al. |
| 2020/0399576 | A1 | 12/2020 | Haneda et al. |
| 2020/0407672 | A1 | 12/2020 | Haneda et al. |
| 2021/0071147 | A1 | 3/2021 | Haneda et al. |
| 2022/0227898 | A1 | 7/2022 | Iguchi et al. |

FOREIGN PATENT DOCUMENTS

| | | |
|---|---|---|
| CN | 1216581 | 5/1999 |
| CN | 101528822 | 9/2009 |
| CN | 104428651 | 3/2015 |
| CN | 107406652 | 11/2017 |
| EP | 0339371 | 11/1989 |
| EP | 0 897 000 | 2/1999 |
| EP | 2 385 105 | 11/2011 |

(Continued)

OTHER PUBLICATIONS

JP H10204204; Published 1998, machine translation.*
Extended European Search Report issued Dec. 23, 2021 in corresponding European Patent Application No. 18893713.0, 7 pages.
Office Action issued Apr. 12, 2023 in U.S. Appl. No. 16/958,218, 18 pages.
Office Action issued Sep. 21, 2022 in U.S. Appl. No. 16/958,218, 15 pages.
Extended European Search Report issued Oct. 12, 2021 in corresponding European Patent Application No. 18893580.3, 8 pages.
Translation of The International Preliminary Report on Patentability issued Jul. 9, 2020 in International (PCT) Application No. PCT/JP2018/048389.
Translation of The International Preliminary Report on Patentability issued Jul. 2, 2020 in International (PCT) Application No. PCT/JP2018/048386.
Translation of The International Preliminary Report on Patentability issued Jul. 9, 2020 in International (PCT) Application No. PCT/JP2018/048391.

(Continued)

*Primary Examiner* — Jennifer M. H. Tichy
(74) *Attorney, Agent, or Firm* — Wenderoth, Lind & Ponack, L.L.P.

(57) ABSTRACT

A scaffolding material for cell culture, which has a dispersion component $\gamma^d$ of the surface free energy of 24.5 mJ/m$^2$ or more and less than 45.0 mJ/m$^2$, and a dipole component $\gamma^p$ of the surface free energy of 1.0 mJ/m$^2$ or more and less than 20.0 mJ/m$^2$. According to the scaffolding material for cell culture, the scaffolding material can have suitable hydrophilicity and strength, high fixation of cells after seeding, and highly efficient cell proliferation.

10 Claims, 9 Drawing Sheets

(56) References Cited

FOREIGN PATENT DOCUMENTS

| | | |
|---|---|---|
| EP | 2 821 789 | 1/2015 |
| EP | 3 733 834 | 11/2020 |
| EP | 4 286 508 | 12/2023 |
| JP | 6-153905 | 6/1994 |
| JP | 9-131397 | 5/1997 |
| JP | 10-52268 | 2/1998 |
| JP | 10-204204 | 8/1998 |
| JP | 2001-89574 | 4/2001 |
| JP | 2001-131325 | 5/2001 |
| JP | 2006-42758 | 2/2006 |
| JP | 2006-272002 | 10/2006 |
| JP | 2006-314285 | 11/2006 |
| JP | 2009-39138 | 2/2009 |
| JP | 2009-273444 | 11/2009 |
| JP | 2010-91689 | 4/2010 |
| JP | 2010-158180 | 7/2010 |
| JP | 2010-168444 | 8/2010 |
| JP | 4956753 | 6/2012 |
| JP | 2015-142525 | 8/2015 |
| JP | 2015-195752 | 11/2015 |
| JP | 2015-199932 | 11/2015 |
| JP | 2015-205462 | 11/2015 |
| JP | 2016-186044 | 10/2016 |
| JP | 2017-23008 | 2/2017 |
| JP | 2017-46676 | 3/2017 |
| JP | 6144437 | 6/2017 |
| JP | 2017-163898 | 9/2017 |
| JP | 6427450 | 11/2018 |
| JP | 2019-115322 | 7/2019 |
| JP | 2019-115323 | 7/2019 |
| JP | 2019-118345 | 7/2019 |
| KR | 2007-0122519 | 12/2007 |
| TW | 201540829 | 11/2015 |
| WO | 97/41216 | 11/1997 |
| WO | 01/05877 | 1/2001 |
| WO | 2006/093207 | 9/2006 |
| WO | 2012/023518 | 2/2012 |
| WO | 2013/183777 | 12/2013 |
| WO | 2015/129837 | 9/2015 |
| WO | 2016/122123 | 8/2016 |
| WO | 2017/057663 | 4/2017 |
| WO | 2019/131978 | 7/2019 |
| WO | 2019/131981 | 7/2019 |
| WO | 2019/131982 | 7/2019 |

OTHER PUBLICATIONS

Office Action dated Mar. 31, 2022 in corresponding U.S. Appl. No. 16/958,218, filed Jun. 26, 2020, 19 pages.
First Examination Report issued Jun. 14, 2022 in corresponding Indian Patent Application No. 202047029411, 7 pages.
Extended European Search Report issued Oct. 8, 2021 in corresponding European Patent Application No. 18897018.0, 8 pages.
International Search Report issued Mar. 26, 2019 in International (PCT) Application No. PCT/JP2018/048386.
Bayramoglu et al., "Preparation and Characterization of Poly(hydroxyethyl methacrylate-co-poly(ethyl-eneglycol-methacrylate)/Hydroxypropyl-chitosan) Hydrogel Films: Adhesion of Rat Mesenchymal Stem Cell," Macromolecular Research, 2011, vol. 19, No. 4, pp. 385-395.
Rebollar et al., "Physicochemical modifications accompanying UV laser induced surface structures on poly(ethyleneterephthalate) and their effect on adhesion of mesenchymal cell," Phys. Chem. Chem. Phys., 2014, vol. 16, pp. 17551-17559.
Togami et al., "Effects of water holding capability of the PVF sponge on the adhesion and differentiation of rat bone marrow stem cell culture," Society For Biomaterials, 2013, vol. 102A, No. 1, pp. 247-253.
Saha et al., "Surface-engineered substrates for improved human pluripotent stem cell culture under fully defined conditions," PNAS, 2011, vol. 108, No. 46, pp. 18714-18719.
Tunma et al., "Improving the attachment and proliferation of umbilical cord mesenchymal stem cells on modified polystyrene by nitrogen-containing plasma," Cytotechnology, 2013, vol. 65, pp. 119-134.
Togami et al., "Effects of the water-holding capability of polyvinyl formal sponges on osteogenic ability in in vivo experiments," Society For Biomaterials, 2014, vol. 103B Issue 1, pp. 188-194.
Miyoshi et al., "Three-dimensional culture of mouse bone marrow cells within a porous polymer scaffold: effects of oxygen concentration and stromal layer on expansion of haematopoietic progenitor cells," Journal of Tissue Engineering and Regenerative Medicine, 2011, vol. 5, pp. 112-118.
Notice of Ground of Rejection mailed on Apr. 14, 2020 in Japanese Patent Application No. 2019-562491 with English-language translation.
Office Action issued Feb. 10, 2023 in U.S. Appl. No. 16/919,452, 23 pages.
Office Action issued Jan. 20, 2023 in U.S. Appl. No. 16/958,204, 22 pages.
Office Action issued Jan. 26, 2023 in U.S. Appl. No. 16/958,182, 28 pages.
Poly(vinylamine), Polymer source, Inc., downloaded on Jan. 19, 2023 from www.polymersource.ca/index.php?route=product, one page (Year: 2023).
Examination report issued Nov. 16, 2023 in corresponding Australian Patent Application No. 2018398050, 3 pages.
Office Action issued Jun. 27, 2023 in U.S. Appl. No. 16/958,182, 18 pages.
Lee et al., "Cell Behavior on Polymer Surfaces With Different Functional Groups", Science and Technology of Polymers and Advanced Materials, Edited by P.N. Prasad et al., Plenum Press, New York, p. 535-545 (Year: 1998), 11 pages.
Official Communication dated Sep. 18, 2023 issued in corresponding Indian Patent Application No. 202047029416, 2 pages.
Extended European Search Report issued Jan. 31, 2024 in corresponding European Patent Application No. 23203425.6.
Office Action issued Oct. 13, 2023 in U.S. Appl. No. 16/958,218.
Examination report No. 1 issued Nov. 1, 2023 in Australian Patent Application No. 2018398052.
Office Action issued Nov. 21, 2023 in corresponding U.S. Appl. No. 16/919,452.
Meng Zhong Wang., "Handbook of Adhesive Application", p. 16-20, Chemical Industry Press, publication date: Nov. 30, 1987.
Office Action issued Jun. 22, 2023 in U.S. Appl. No. 16/919,452, 13 pages.
Office Action issued Aug. 14, 2023 in corresponding U.S. Appl. No. 16/958,204.
English Translation of Meng Zhong Wang, "Handbook of Adhesive Application", Chemical Industry Press, publication date: Nov. 30, 1987, pp. 16-20, previously cited in the PTO/SB/08 submitted Dec. 19, 2023.
Office Action issued May 8, 2024 in related U.S. Appl. No. 16/958,218, 20 pages.
Office Action issued Jun. 17, 2024 in U.S. Appl. No. 16/958,204, 15 pages.
Chen Huipeng (ed.), "Advances in Pharmaceutical Bioengineering", People's Military Medical Press, Jul. 2004, p. 259, with English-language translation.
Wang Yingjun (ed), "Biomedical Ceramic Materials", South China University of Technology Press, Oct. 2010, pp. 167-168, with English-language translation.
Office Action issued Oct. 4, 2024 in U.S. Appl. No. 16/958,218.

* cited by examiner

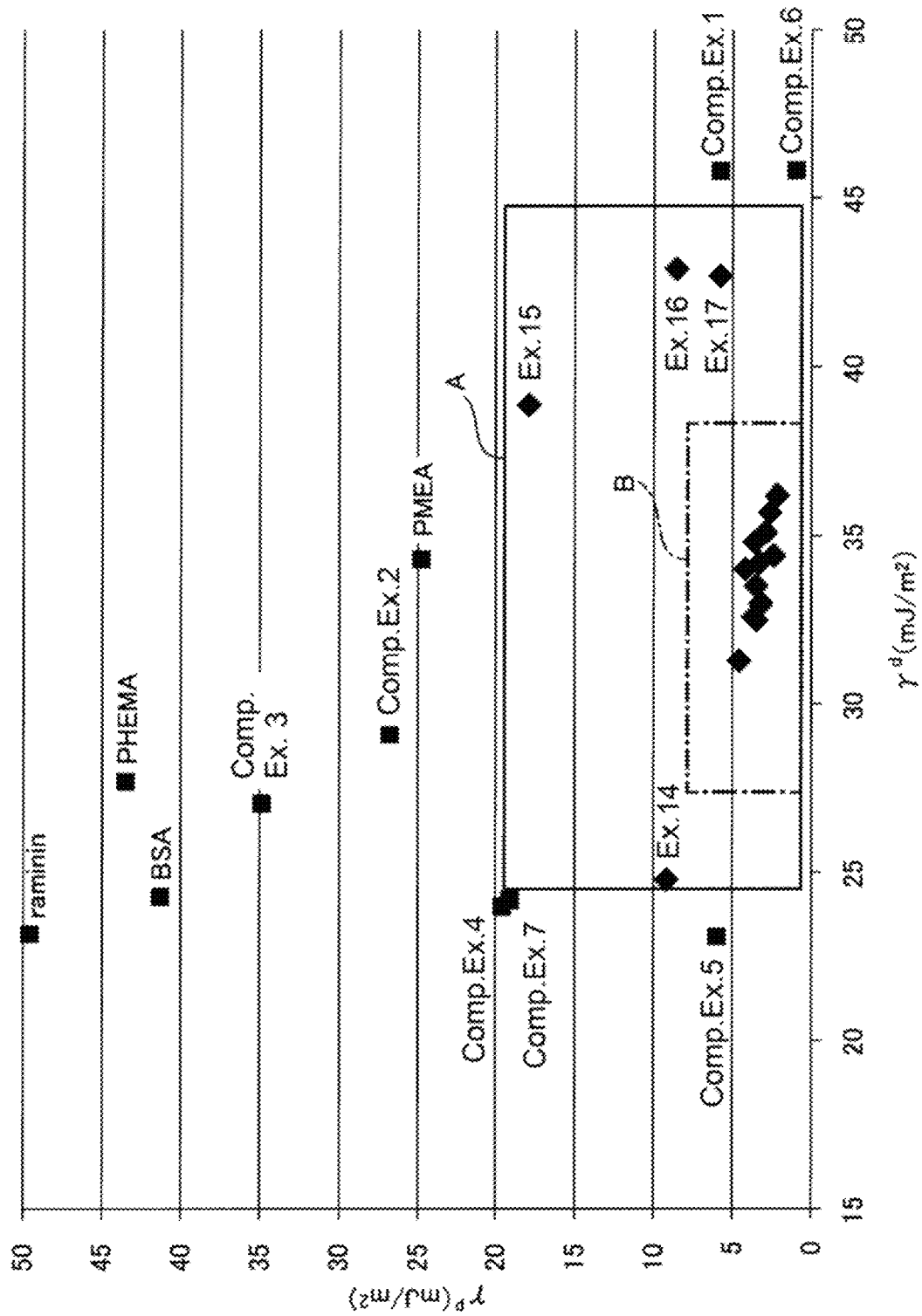

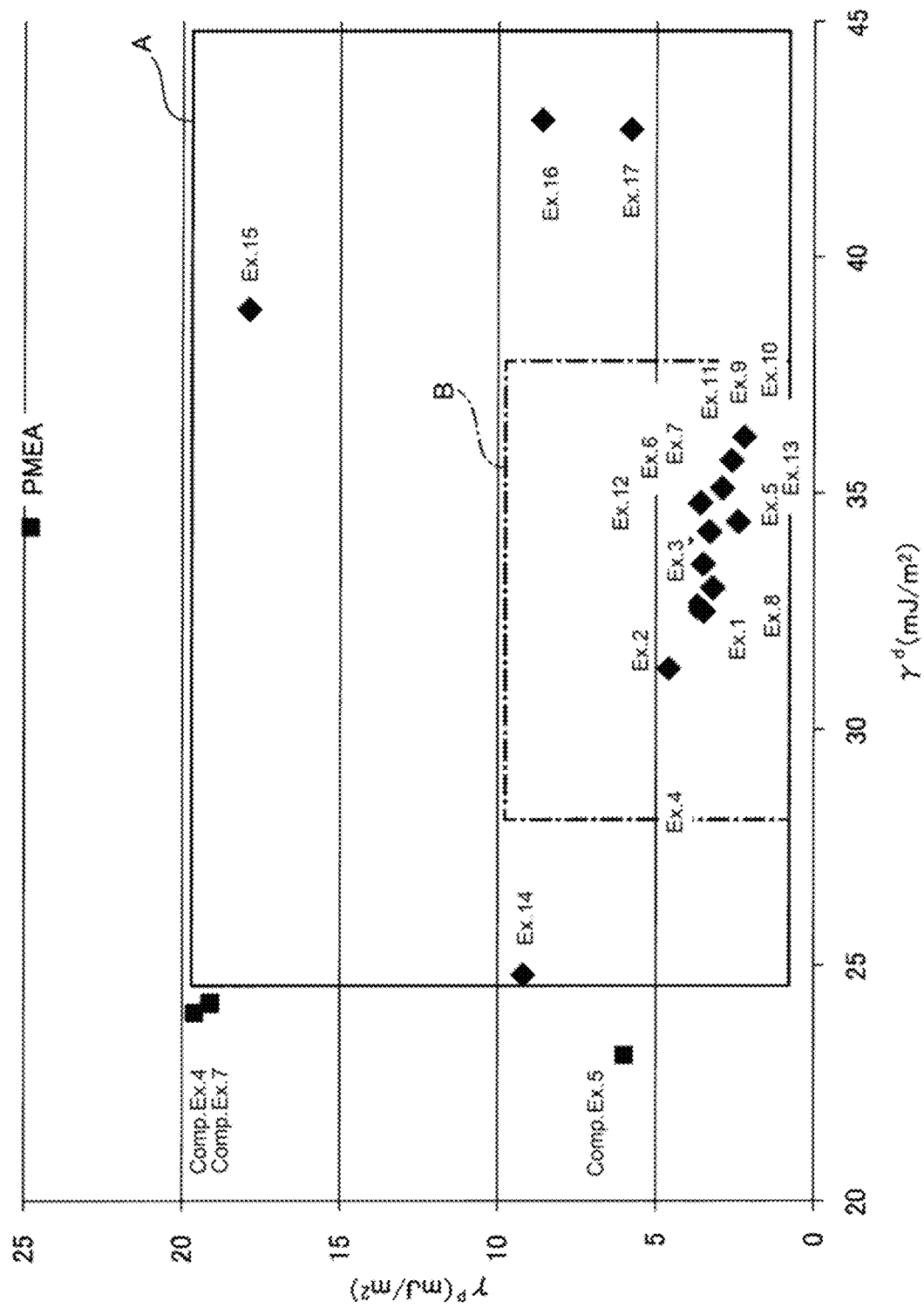

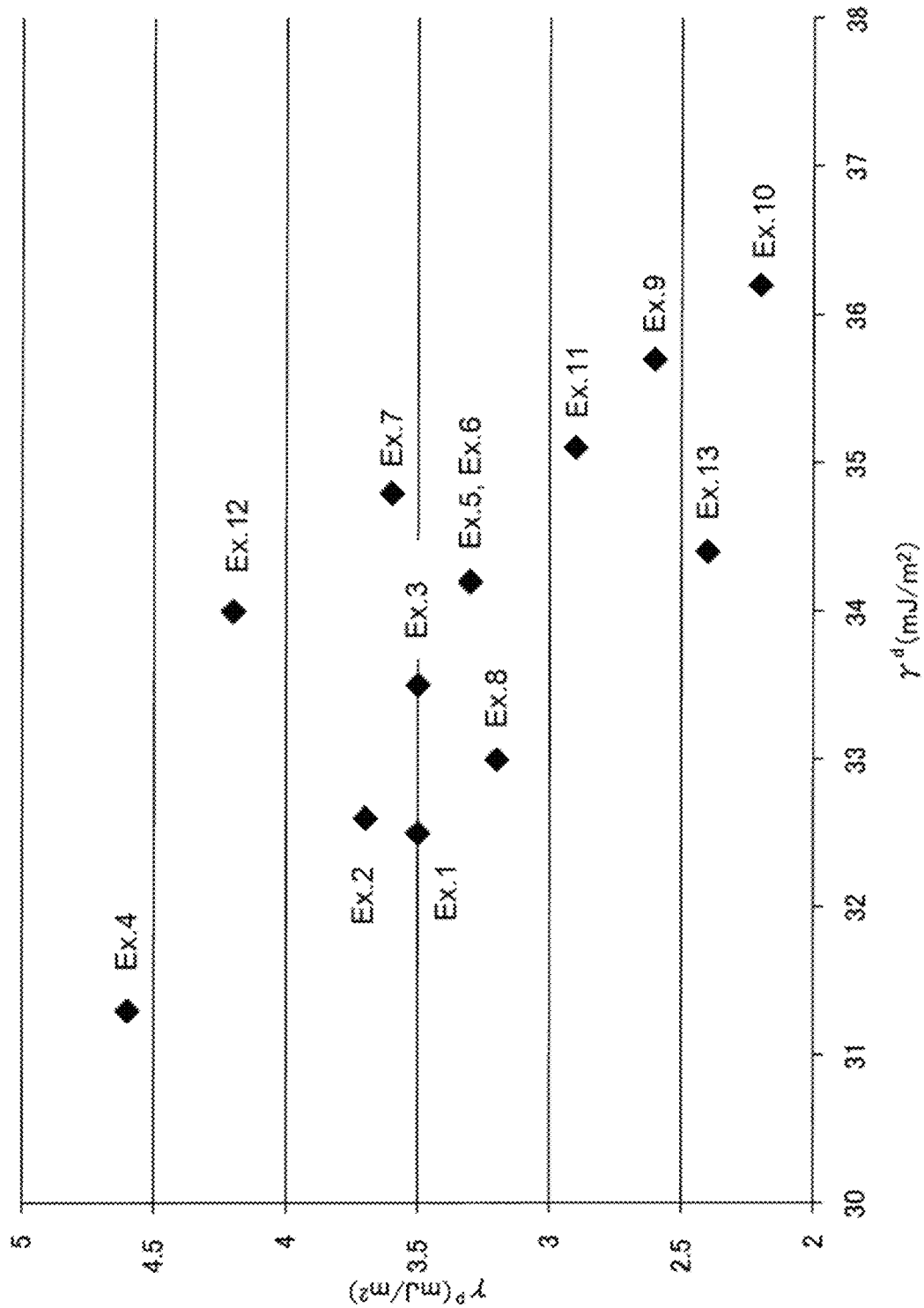

[FIG. 4]
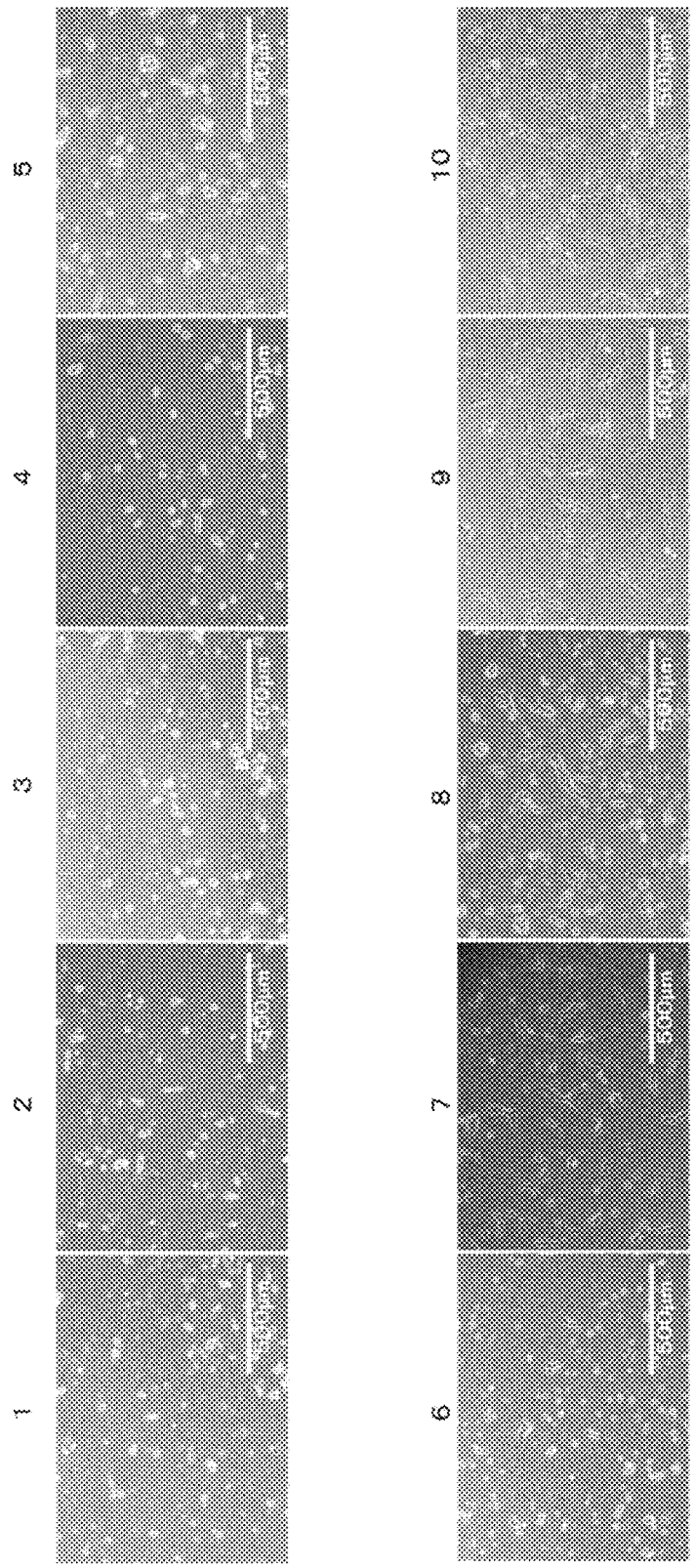

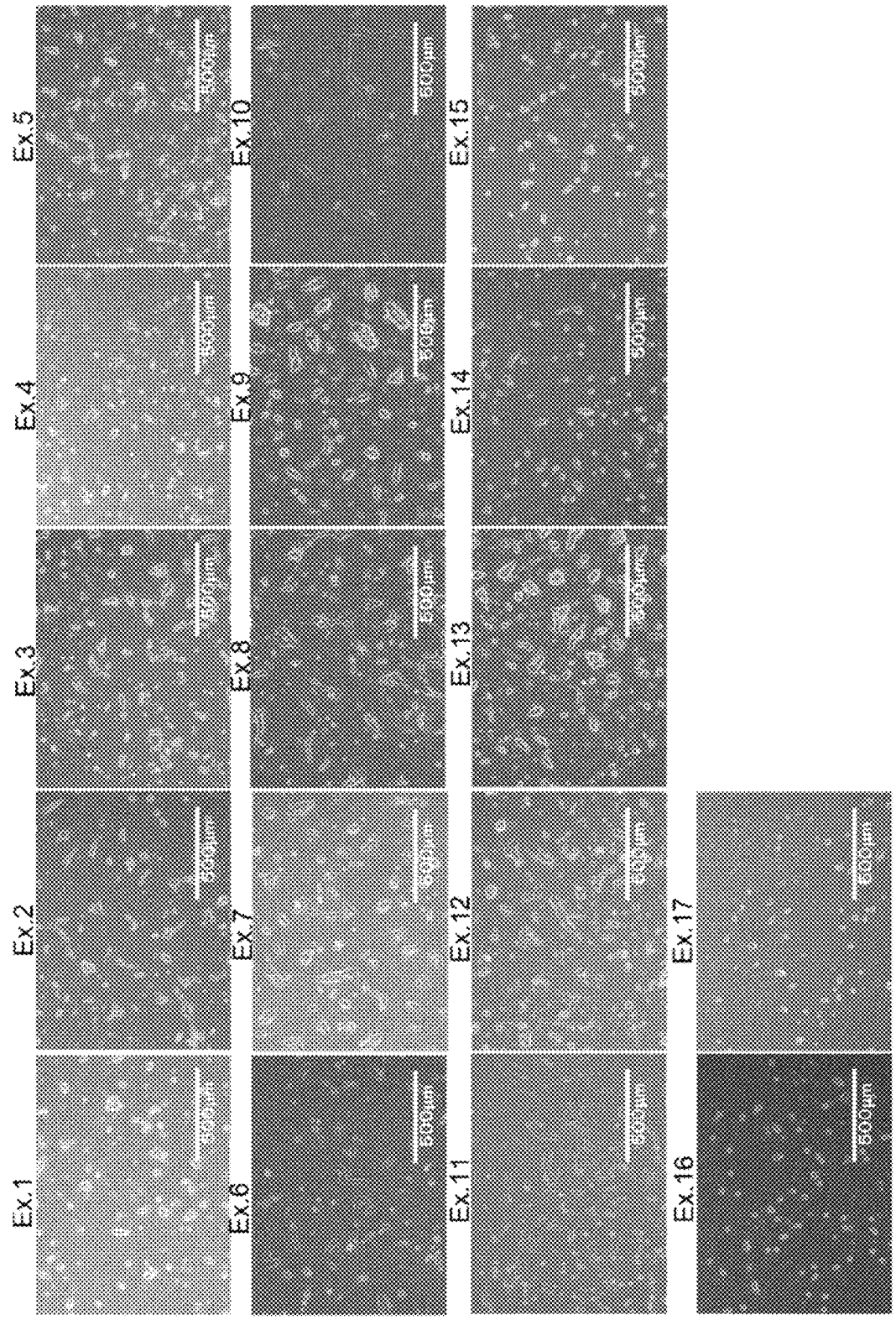
[FIG. 5]

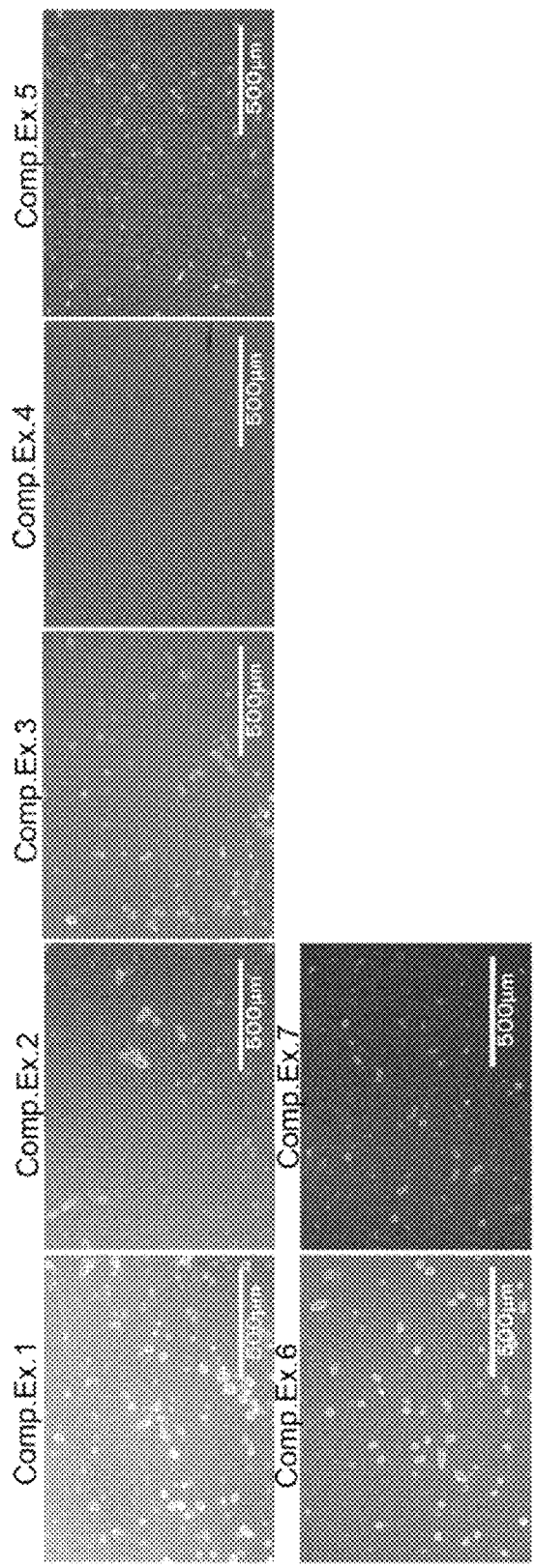
[FIG. 6]

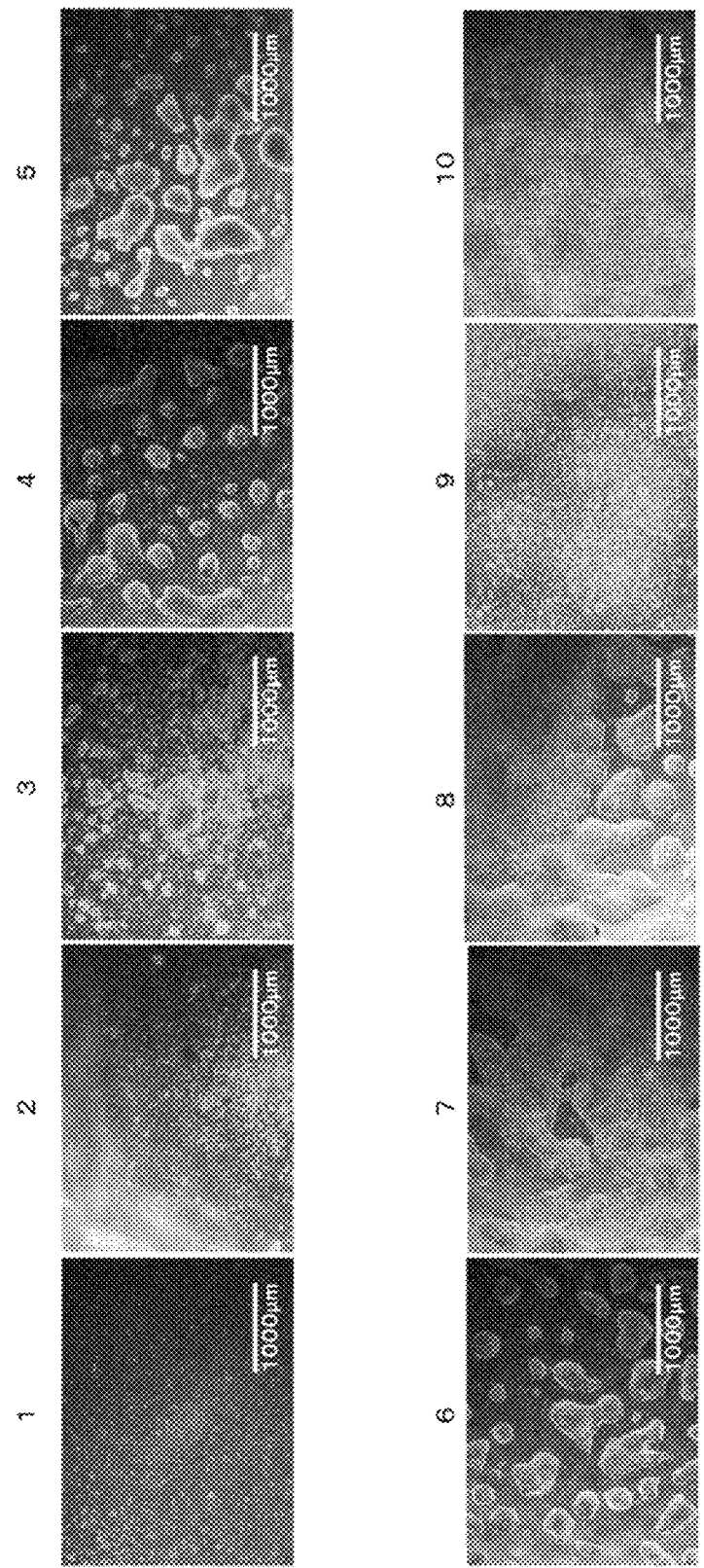
[FIG. 7]

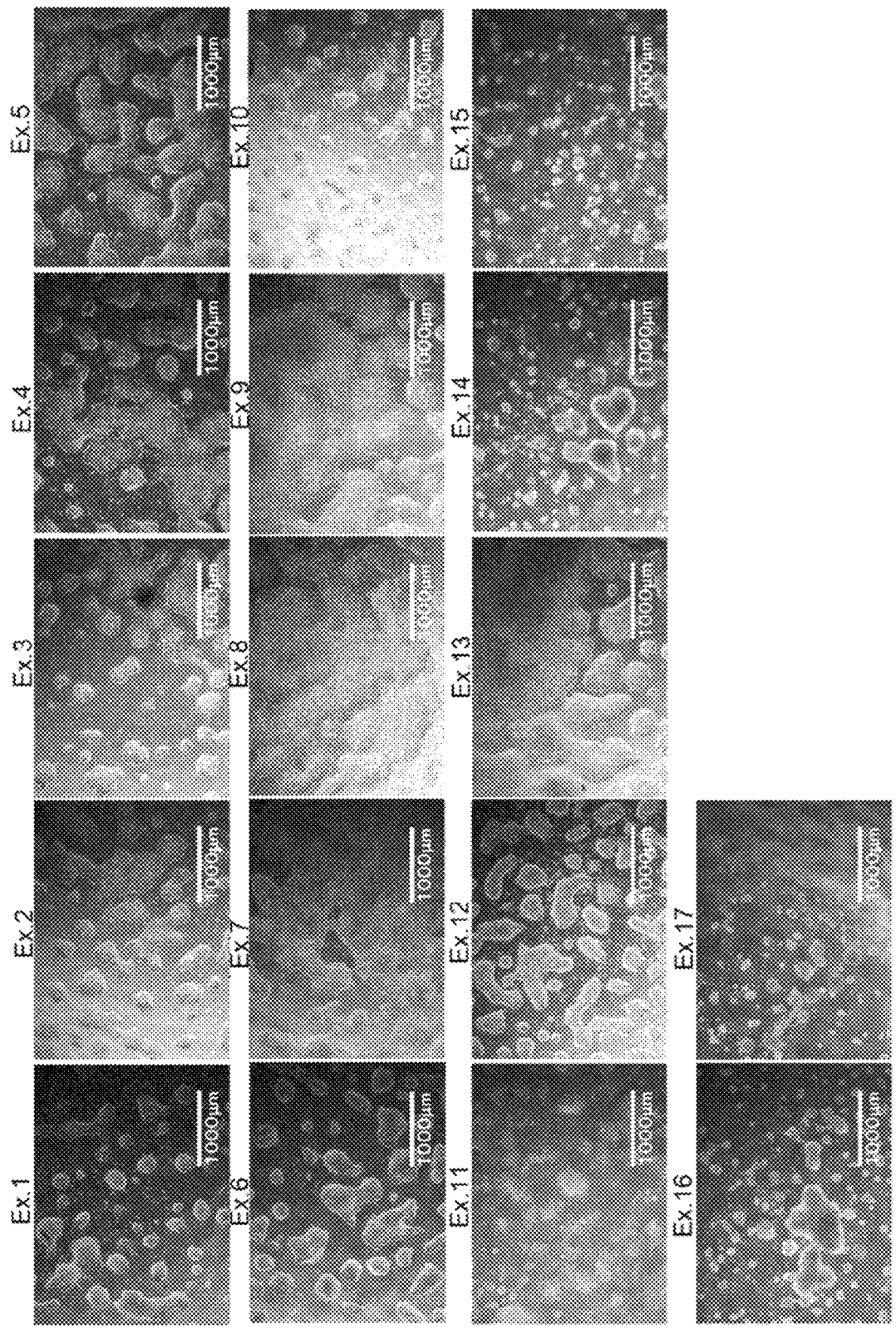
[FIG. 8]

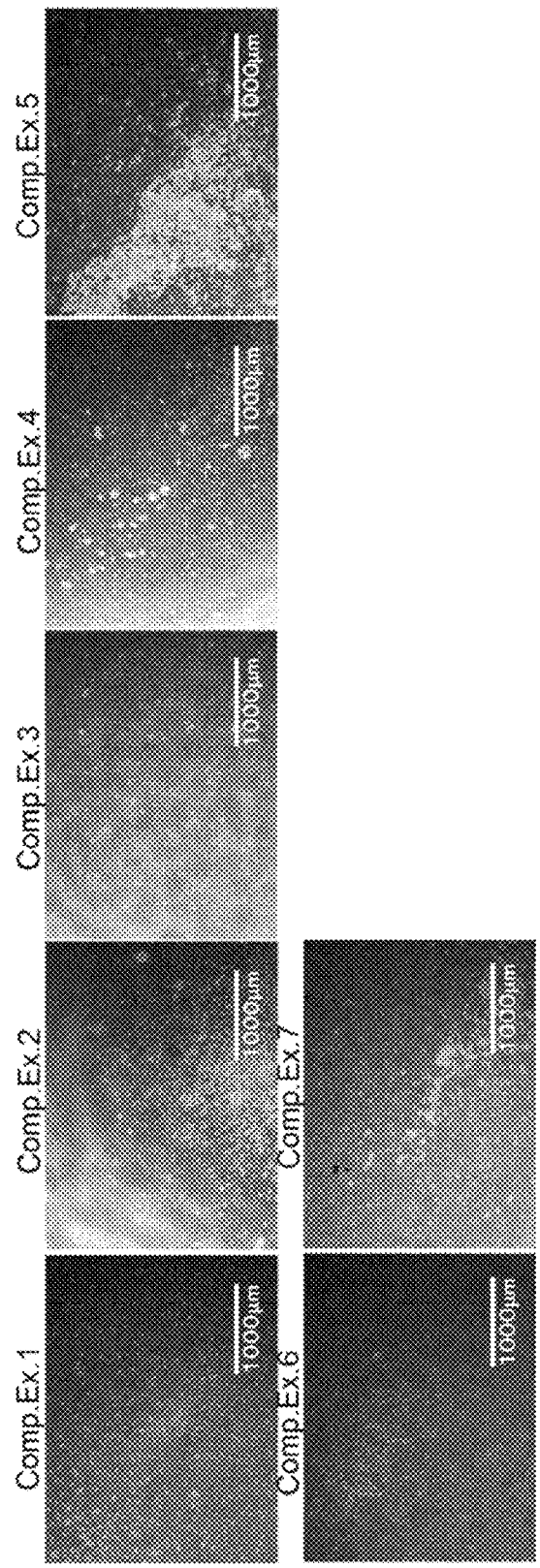
[FIG. 9]

SCAFFOLDING MATERIAL FOR CELL CULTURES AND CELL CULTURE METHOD USING SAME

BACKGROUND OF THE INVENTION

Field of the Invention

The present invention relates to a scaffolding material for cell culture and a cell culture method using the same.

Description of the Related Art

Stem cells are expected to be applied on drug discovery and regenerative medicine. Stem cells are cells that have self-renew potency and differentiation potency, including pluripotent stem cells that can differentiate into all cell types, and tissue stem cells and tissue progenitor cells that can differentiate only into constituent cell types of the body tissue in the same series. Examples of the pluripotent stem cells include human pluripotent stem cells (hPSCs) such as human embryonic stem cells (hESCs) and human induced pluripotent stem cells (hiPSCs). It is an essential basic technology to cultivate and proliferate stem cells safely and with good reproducibility for medical application of these cells. In particular, for industrial application on regenerative medicine, it is necessary to handle a large amount of stem cells in an undifferentiated state. Accordingly, extensive studies have been conducted on techniques for proliferating stem cells using natural and synthetic macromolecules and feeder cells, and maintaining the pluripotency (or multipotency). In particular, it is known that cell fixation after seeding is extremely high when an adhesive protein such as laminin or vitronectin, or a matrigel derived from mouse sarcoma is used as a natural polymer.

However, there are problems in that natural polymers are expensive because of their very low productivity, variations between lots can be seen because they are naturally occurring substances, and there are safety concerns due to animal-derived components.

In order to solve the above problems, a stem cell culture resin carrier using a synthetic resin has been proposed. For example, the column of Examples in Patent Document 1 discloses a polyvinyl acetal compound having a degree of acetalization of 20 to 60 mol % in order to provide a scaffold having excellent hydrophilicity and water resistance in culturing mouse fibroblasts. The column of Examples in Patent Document 2 discloses a hydrogel composed of an acrylic polymer in culturing mouse ES cells. The column of Examples in Patent Document 3 discloses a hydrophilic and flexible polyrotaxane gel in culturing mouse iPS cells.

RELATED ART DOCUMENT

Patent Document

Patent Document 1: JP 2006-314285 A
Patent Document 2: JP 2010-158180 A
Patent Document 3: JP 2017-23008 A

SUMMARY OF THE INVENTION

Problem to be Solved by the Invention

However, Patent Document 1 has a problem in that the scaffolding material resin is swelled in a medium due to its high hydrophilicity, and thus is peeled off. In addition, there is a problem in that the fixation of stem cells or pluripotent stem cells after seeding is so low that the cells do not proliferate sufficiently. In Patent Document 2, sodium 2-acrylamido-2-methylpropane sulfonate, sodium p-styrene sulfonate and N,N'-dimethylacrylamide are used, so that there is a problem in that the scaffolding material resin is swelled in a medium due to its high hydrophilicity, and thus is peeled off. Patent Document 3 has a problem in that the scaffolding material resin is swelled in a medium due to its high hydrophilicity, and thus is peeled off. In addition, there is a problem in that the scaffolding material is so flexible that differentiation into cardiomyocytes is promoted.

In addition, such a conventional scaffolding material for cell culture has a problem in that even when cells other than stem cells are used, the fixability after seeding is so low that the cells do not proliferate sufficiently.

As described above, there have been needs of a scaffolding material for cell culture having suitable hydrophilicity and strength, and a cell culture method using the same.

An object of the present invention is to provide a scaffolding material for cell culture having suitable hydrophilicity and strength, high fixation of cells after seeding, and highly efficient cell proliferation, and a cell culture method using the same.

Means for Solving the Problems

The present invention relates to the followings.

(1) A scaffolding material for culturing a cell, having a dispersion component $\gamma^d$ of the surface free energy of 24.5 mJ/m$^2$ or more and less than 45.0 mJ/m$^2$, and a dipole component $\gamma^p$ of the surface free energy of 1.0 mJ/m$^2$ or more and less than 20.0 mJ/m.

(2) The scaffolding material for culturing a cell according to (1), containing a synthetic resin.

(3) The scaffolding material for culturing a cell according to (2), in which the synthetic resin contains at least any one of a polyvinyl acetal skeleton and a poly(meth)acrylic ester skeleton.

(4) The scaffolding material for culturing a cell according to (2), in which the synthetic resin is a polyvinyl acetal resin.

(5) The scaffolding material for culturing a cell according to (4), in which the polyvinyl acetal resin contains as a structural unit at least one selected from the group consisting of a structural unit having an amine structure, a structural unit having an imine structure and a structural unit having an amide structure.

(6) The scaffolding material for culturing a cell according to (5), in which the polyvinyl acetal resin has a total content of the structural unit having an amine structure, the structural unit having an imine structure and the structural unit having an amide structure of 0.1 mol % or more and 30 mol % or less.

(7) A scaffolding material for culturing a cell containing a synthetic resin, the synthetic resin containing a polyvinyl acetal resin, and the degree of acetalization of the polyvinyl acetal resin being higher than 60 mol %.

(8) The scaffolding material for culturing a cell according to (7), in which the polyvinyl acetal resin contains as a structural unit at least one selected from the group consisting of a structural unit having an amine structure, a structural unit having an imine structure and a structural unit having an amide structure.

(9) The scaffolding material for culturing a cell according to (8), in which the polyvinyl acetal resin has a total content of the structural unit having an amine structure, the structural unit having an imine structure and the structural unit having an amide structure of 0.1 mol % or more and 30 mol % or less.

(10) A container for culturing a cell, including a resin film made of the scaffolding material for culturing a cell according to (1) on at least a part of a cell culture region.

(11) A container for culturing a cell, including a resin film made of the scaffolding material for culturing a cell according to (7) on at least a part of a cell culture region.

(12) A fiber for culturing a cell, including the scaffolding material for culturing a cell according to (1).

(13) A fiber for culturing a cell, including the scaffolding material for culturing a cell according to (7).

(14) A method for culturing a cell, using the scaffolding material according to (1).

(15) A method for culturing a cell, using the scaffolding material according to (7).

(16) The method for culturing a cell according to (14), including a step of seeding a cell mass on the scaffolding material.

(17) The method for culturing a cell according to (15), including a step of seeding a cell mass on the scaffolding material.

Effect of the Invention

According to the present invention, there are provided a scaffolding material for cell culture having suitable hydrophilicity and strength, and high fixation of cells after seeding, and a cell culture method using the same.

BRIEF DESCRIPTION OF THE DRAWINGS

FIG. 1 is a view summarizing the relationship of $\gamma^p$ to $\gamma^d$ of main synthetic resins;

FIG. 2 is a partially enlarged view of FIG. 1;

FIG. 3 is a partially enlarged view of FIG. 1;

FIG. 4 is a view showing evaluation criteria for initial adhesion 24 hours after cell seeding;

FIG. 5 is phase contrast micrographs in the scaffolding materials for cell culture according to Examples 24 hours after iPS cell seeding;

FIG. 6 is phase contrast micrographs in the scaffolding materials for cell culture according to Comparative Examples 24 hours after iPS cell seeding;

FIG. 7 is a view showing evaluation criteria for cell proliferation 5 days after cell seeding;

FIG. 8 is phase contrast micrographs in the scaffolding materials for cell culture according to Examples 5 days after iPS cell seeding; and FIG. 9 is phase contrast micrographs in the scaffolding materials for cell culture according to Comparative Examples 5 days after iPS cell seeding.

DETAILED DESCRIPTION OF THE PREFERRED EMBODIMENTS

Hereinafter, a description is made of the present invention with reference to embodiments, but the present invention is not limited to the following embodiments.

[Scaffolding Material for Cell Culture 1]

In order to solve the above problems, the present inventors have found that the above problems can be solved by controlling the surface free energy of a scaffolding material for cell culture, and thus have completed the present invention. In other words, a first aspect of the present invention relates to a scaffolding material for cell culture in which the dispersion component $\gamma^d$ and the dipole component $\gamma^p$ of the surface free energy are within a certain range.

Note that the dispersion component $\gamma^d$ and the dipole component $\gamma^p$ of the surface free energy in this specification can be measured using the Kaelble-Uy theoretical formula.

Here, the Kaelble-Uy theoretical formula is based on the assumption that the total surface free energy $\gamma$ is composed of the sum of the dispersion component $\gamma^d$ and the dipole component $\gamma^p$, as represented by equation (1).

[Equation 1]

$$\gamma = \gamma^d + \gamma^p \tag{1}$$

In addition, when the surface free energy of the liquid surface is represented by $\gamma_d$ (mJ/m$^2$), the surface free energy of the solid is represented by $\gamma_p$ (mJ/m$^2$), and the contact angle is represented by $\theta(°)$, the following equation (2) is established.

[Equation 2]

$$\gamma_l(1+\cos\theta) = 2\sqrt{\gamma_s^d \gamma_l^d} + 2\sqrt{\gamma_s^p \gamma_l^p} \tag{2}$$

Accordingly, using two types of liquids (pure water and diiodomethane in the present invention) with known components of $\gamma^d$, the dispersion component $\gamma^d$ and the dipole component $\gamma^p$ of a scaffolding material for cell culture (a resin film formed using a scaffolding material for cell culture) are determined by measuring each contact angle $\theta$ with respect to the scaffolding material for cell culture and solving simultaneous equations for $\gamma_s^d$ and $\gamma_s^p$.

The contact angle of pure water can be obtained by dropping 1 µL of pure water onto a scaffolding material for cell culture (a resin film formed using a scaffolding material for cell culture) and then photographing the droplet image after 30 seconds using a contact angle meter (manufactured by Kyowa Interface Science, Inc., DMo-701). In addition, the contact angle of diiodomethane can be obtained by dropping 1 µL of diiodomethane onto a scaffolding material for cell culture (a resin film formed using a scaffolding material for cell culture) and then similarly photographing the droplet image after 30 seconds.

The scaffolding material for cell culture preferably contains a synthetic resin from the viewpoint of suitably adjusting the dispersion component $\gamma^d$ and the dipole component $\gamma^p$ of the surface free energy. In addition, the synthetic resin preferably contains at least any one of a polyvinyl acetal skeleton and a poly(meth)acrylic ester skeleton from the viewpoint of suitably adjusting the dispersion component $\gamma^d$ and the dipole component $\gamma^p$ of the surface free energy.

FIG. 1 is a view summarizing the relationship between the dipole component $\gamma^p$ and the dispersion component $\gamma^d$ of the surface free energy of main synthetic resins. Each of FIGS. 2 and 3 is a partially enlarged view of FIG. 1. In addition, in FIGS. 1 to 3, the results of the synthetic resins used in Examples and Comparative Examples described below are also shown.

The dispersion component $\gamma^d$ of the surface free energy of the scaffolding material for cell culture of the present invention is 24.5 mJ/m$^2$ or more and less than 45.0 mJ/m$^2$. The dispersion component $\gamma^d$ is more preferably 28.0 mJ/m$^2$ or more and 38.0 mJ/m$^2$ or less, still more preferably 32.8 mJ/m$^2$ or more and 36.0 mJ/m$^2$ or less.

The dipole component $\gamma^p$ of the surface free energy of the scaffolding material for cell culture of the present invention is 1.0 mJ/m$^2$ or more and less than 20.0 mJ/m$^2$. The dipole component $\gamma^p$ is more preferably 1.0 mJ/m$^2$ or more and 10.0 mJ/m$^2$ or less, still more preferably 2.5 mJ/m$^2$ or more and 5.0 mJ/m$^2$ or less.

The dispersion component $\gamma^d$ and the dipole component $\gamma^p$ can be controlled, for example, by appropriately changing the skeleton of the synthetic resin described below.

For example, the dispersion component $\gamma^d$ can be increased by increasing the amount of a non-polar functional group in the skeleton of the synthetic resin or by introducing a functional group having a cyclic structure, or can be decreased by reducing the amount of a butyl group component in the synthetic resin, or the like. The synthetic resin preferably contains at least any one of a polyvinyl acetal skeleton and a poly(meth)acrylic ester skeleton.

For example, the dipole component $\gamma^p$ can be increased by increasing the amount of a polar functional group in the skeleton of the synthetic resin or by introducing a functional group having an ether structure, or can be decreased by increasing the amount of a butyl group that is a non-polar functional group.

[Synthetic Resin]

The synthetic resin refers to a resin mainly composed of a polymer (hereinafter, also simply referred to as "polymer") obtained by polymerizing (including polycondensing) a polymerizable monomer (hereinafter, also simply referred to as "monomer"). The polymer may be a homopolymer obtained by polymerizing only one type of monomer, or a copolymer obtained by polymerizing two or more types of monomers.

Examples of the polymer include a polymer composed of one or more polymerizable monomers such as (un)saturated hydrocarbons, aromatic hydrocarbons, (un)saturated fatty acids, aromatic carboxylic acids, (un)saturated ketones, aromatic ketones, (un)saturated alcohols, aromatic alcohols, (un)saturated amines, aromatic amines, (un)saturated thiols, aromatic thiols and organosilicon compounds.

Specific examples of the polymer include polyolefin, polyether, polyvinyl alcohol, polyvinyl acetal, polyester, poly(meth)acrylic ester, epoxy resin, polyamide, polyimide, polyurethane, polycarbonate, cellulose and polypeptide.

From the viewpoint of further enhancing the fixation of cells, the synthetic resin preferably has at least one skeleton of a polyvinyl acetal skeleton and a poly(meth)acrylic ester skeleton, and a polyvinyl acetal resin is preferable.

From the viewpoint of further enhancing the fixation of cells, the polymer is preferably a poly(meth)acrylic ester or a polyvinyl acetal resin, and a polyvinyl acetal resin is more preferable.

These polymers may be used alone or in combination of two or more. When two or more polymers are combined, they may be used as a mixture, or may be used as a polymer in which the skeletons of the two or more polymers are chemically bonded. When two or more polymers are combined as a synthetic resin, it is preferable to combine poly(meth)acrylic ester and polyvinyl acetal.

In the present specification, "(meth)acrylate" refers to at least one selected from the group consisting of (meth)acrylic ester and (meth)acrylic acid. In addition, poly(meth)acrylate is not only polymers obtained by polymerizing a monomer, (meth)acrylic ester or (meth)acrylic acid, but also includes those obtained by copolymerizing a monomer in addition to (meth)acrylic ester or (meth)acrylic acid.

The (meth)acrylic ester is not particularly limited, but includes alkyl (meth)acrylic esters, cyclic alkyl (meth) acrylic esters, aryl (meth)acrylic esters, (meth)acrylamides, polyethylene glycol (meth)acrylates and phosphorylcholine (meth)acrylates.

Examples of the alkyl (meth)acrylic ester include methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-octyl (meth)acrylate, isooctyl (meth)acrylate, 2-ethylhexyl (meth) acrylate, nonyl (meth)acrylate, isononyl (meth)acrylate, decyl (meth)acrylate, isodecyl (meth)acrylate, lauryl (meth) acrylate, stearyl (meth)acrylate and isotetradecyl (meth) acrylate.

These alkyl (meth)acrylic esters are not particularly limited, but may be substituted with various substituents including an alkoxy group having 1 to 3 carbon atoms and a tetrahydrofurfuryl group. Examples include methoxyethyl acrylate and tetrahydrofurfuryl acrylate.

Examples of the cyclic alkyl (meth)acrylic ester include cyclohexyl (meth)acrylate and isobornyl (meth)acrylate.

Examples of the aryl (meth)acrylic ester include phenyl (meth)acrylate and benzyl (meth)acrylate.

Examples of the acrylamide include (meth)acrylamide, N-isopropyl (meth)acrylamide, N-tert-butyl (meth)acrylamide, N,N'-dimethyl (meth)acrylamide, (3-(meth)acrylamidopropyl) trimethylammonium chloride, 4-(meth)acryloylmorpholine, 3-(meth)acryloyl-2-oxazolidinone, N-[3-(dimethylamino) propyl](meth)acrylamide, N-(2-hydroxyethyl) (meth)acrylamide, N-methylol (meth) acrylamide and 6-(meth)acrylamidohexanoic acid.

Examples of the polyethylene glycol (meth)acrylate include methoxy-polyethylene glycol (meth)acrylate, ethoxy-polyethylene glycol (meth)acrylate, hydroxy-polyethylene glycol (meth)acrylate, methoxy-diethylene glycol (meth)acrylate, ethoxy-diethylene glycol. (meth)acrylate, hydroxy-diethylene glycol (meth)acrylate, methoxy-triethylene glycol (meth)acrylate, ethoxy-triethylene glycol (meth)acrylate and hydroxy-triethylene glycol (meth)acrylate.

Examples of the phosphorylcholine (meth)acrylate include 2-(meth)acryloyloxyethyl phosphorylcholine.

Monomers other than the (meth)acrylic esters are not particularly limited, but include (meth)acrylic acids, ethylene and vinyl esters.

The (meth)acrylic esters may be used alone or in combination of two or more.

In this specification, the (meth)acrylic acid is a generic term for acrylic acid and methacrylic acid, and the (meth) acrylate is a generic term for acrylate and methacrylate.

The first aspect of the present invention is preferably a combined one with the second aspect described below from the viewpoint of enhancing the fixation of cells.

[Scaffolding Material for Cell Culture 2]

As a result of intensive studies, the present inventors have found that the above problems can be solved by using a synthetic resin containing a polyvinyl acetal resin, and thus have completed the present invention.

A second aspect of the present invention relates to a scaffolding material for cell culture containing a synthetic resin, wherein the synthetic resin contains a polyvinyl acetal resin, and the degree of acetalization of the polyvinyl acetal resin is higher than 60 mol %. The scaffolding material for cell culture of the present invention includes an aspect composed of only a polyvinyl acetal resin having a degree of acetalization higher than 60 mol %.

The scaffolding material for cell culture has so suitable hydrophilicity and strength that the fixation of cells after seeding is improved. In particular, in a serum-free medium culture containing no feeder cell or adhesive protein, the initial fixation rate of cells after seeding is improved.

Conventionally, it has not been reported to set the degree of acetalization of a synthetic resin higher than 60 mol % when the synthetic resin is used as a scaffolding material for cell culture. This is because there has been a concern about a decrease in the proportion of hydroxyl groups with an increase in the degree of acetalization, which decrease reduces the hydrophilicity of a resin, leading to a decreased fixation of cells after seeding to a scaffolding material for cell culture, or a decrease in permeability of polysaccharides necessary for cell culture and the like. However, the present inventors have found that strength is more important than hydrophilicity, and improving the strength of a scaffolding material for cell culture by setting the degree of acetalization to be higher than 60 mol % allows the fixation of cells after seeding to be improved, and thus have completed the present invention.

Hereinafter, a detailed description is made of the polyvinyl acetal resin.

(Polyvinyl Acetal Resin)

The polyvinyl acetal resin is a resin synthesized by acetalizing polyvinyl alcohol with an aldehyde, which resin has an acetyl group, a hydroxyl group and an acetal group on the side chain.

The lower limit of the degree of acetalization of the polyvinyl acetal resin is preferably 60 mol %, and the upper limit thereof is preferably 90 mol %. When the degree of acetalization is 60 mol % or more, the fixation of cells is excellent, and thus cell proliferation can be performed with high efficiency. When the degree of acetalization is 90 mol % or less, the solubility in solvent can be better. The lower limit is more preferably 65 mol %, and the upper limit is more preferably 85 mol %.

The degree of acetalization of the polyvinyl acetal resin can be measured by $^1$H-NMR measurement.

The aldehydes for use in acetalization include aldehydes having a chain aliphatic group, a cyclic aliphatic group or an aromatic group having 1 to 10 carbon atoms. As the aldehydes, conventionally publicly known aldehydes can be used.

The type of the aldehyde is not particularly limited, but includes formaldehyde, acetaldehyde, propionaldehyde, butyraldehyde, pentanal, hexanal, heptanal, octanal, nonanal, decanal, acrolein, benzaldehyde, cinnamaldehyde, peryladehyde, formylpyridine, formylimidazole, formylpyrrole, formylpiperidine, formylpiperidine, formyltriazole, formyltetrazole, formylindole, formylisoindole, formylpurine, formylbenzimidazole, formylbenzotriazole, formylquinoline, formylisoquinoline, formylquinoxaline, formylcinnoline, formylpteridine, formylfuran, formyloxolane, formyloxane, formylthiophene, formylthiolane, formylthiane, formyladenine, formylguanine, formylcytosine, formylthymine and formyluracil. The aldehyde may be a chain or cyclic one.

The aldehyde is preferably formaldehyde, acetaldehyde, propionaldehyde, butyraldehyde or pentanal, more preferably butyraldehyde. Accordingly, the polyvinyl acetal resin is more preferably a polyvinyl butyral resin.

The lower limit of the average degree of polymerization of the polyvinyl acetal resin is preferably 100, more preferably 200, still more preferably 500, even more preferably 1500. When the average degree of polymerization is in the above range, the strength of the scaffolding material can be suitably maintained even when swelled in a medium to be used for cell culture, so that the cell proliferation is improved. The upper limit of the average degree of polymerization is preferably 6000, more preferably 3000, still more preferably 2500. When the average degree of polymerization is in the above range, the handleability is good and the scaffolding material can be suitably molded.

The polyvinyl alcohol may be a copolymer with a vinyl compound. The polyvinyl acetal resin may be a resin in which a vinyl compound is copolymerized. The polyvinyl acetal resin may be a copolymer with a vinyl compound. In the present invention, as the polyvinyl acetal resin, a polyvinyl acetal resin obtained by copolymerization with a vinyl group is also considered. The vinyl compound is a compound having a vinyl group ($H_2C=CH-$). The vinyl compound may be a polymer having a constitutional unit having a vinyl group.

The copolymer may be a block copolymer of a polyvinyl acetal resin and a vinyl compound, or a graft copolymer in which a vinyl compound is grafted to a polyvinyl acetal resin. The copolymer is preferably a graft copolymer. The copolymer can be synthesized, for example, by any of the following methods (1) to (3). (1) A method for synthesizing a polyvinyl acetal resin including using polyvinyl alcohol in which a vinyl compound is copolymerized. (2) A method for synthesizing a polyvinyl acetal resin including using polyvinyl alcohol and polyvinyl alcohol in which a vinyl compound is copolymerized. (3) A method including graftcopolymerizing a vinyl compound to a pre-graftcopolymerized polyvinyl acetal resin.

The vinyl compound includes ethylene, allylamine, vinylpyrrolidone, maleic anhydride, maleimide, itaconic acid, (meth)acrylic acid, vinylamine and (meth)acrylic ester. The vinyl compound may be used alone or in combination of two or more. Examples of the (meth)acrylic ester include the above-mentioned (meth)acrylic esters.

The graft copolymer contains a graft copolymer having a "unit composed of polyvinyl acetal" and a "unit composed of a vinyl compound" (hereinafter, also simply referred to as "graft copolymer"). The vinyl compound refers to a compound having a structural unit having an ethenyl group ($H_2C=CH-$).

In the present invention, the "unit composed of polyvinyl acetal" and the "unit composed of a vinyl compound" refer to a unit composed of "polyvinyl acetal" and "a vinyl compound" present in the graft copolymer.

In addition, a graft copolymer having a unit composed of polyvinyl acetal and a unit composed of a vinyl compound refers to a branched copolymer in which, to a "unit composed of polyvinyl acetal" or a "unit composed of a vinyl compound" composing the main chain, a "unit composed of polyvinyl acetal" or a "unit composed of a vinyl compound" composing a side chain different from the main chain is bonded.

The molecular weight of the graft copolymer is not particularly limited, but it is preferable that the number average molecular weight (Mn) be 10,000 to 600,000, the weight average molecular weight (Mw) be 20,000 to 1,200,000 and the ratio (Mw/Mn) be 2.0 to 40. When the Mn, Mw and Mw/Mn are in such ranges, the strength of the scaffolding material for cell is suitably maintained.

Examples of the method for measuring the degree of acetalization in the graft copolymer include a method for measuring the degree of acetalization by $^1$H-NMR measurement in which a soluble component of the graft copolymer in xylene is dissolved in deuterated dimethyl sulfoxide.

The polyvinyl acetal resin preferably has on its part a Bronsted basic group or a Bronsted acidic group, more preferably has a Bronsted basic group. In other words, a part of the polyvinyl acetal resin is preferably modified with a Bronsted basic group or a Bronsted acidic group, more preferably modified with a Bronsted basic group. When a part of the polyvinyl acetal resin is modified with a Bronsted basic group or a Bronsted acidic group, in serum-free medium culture containing no feeder cell or adhesive protein, the initial fixation rate after cell seeding is improved and the cell culture becomes easier.

In the present specification, a polyvinyl acetal resin having a Bronsted basic group or a Bronsted acidic group on a part of the polyvinyl acetal resin is sometimes referred to as a modified polyvinyl acetal resin.

The Bronsted basic group is a generic term for a functional group that can receive a hydrogen ion $H^+$ from another substance. Examples of the Bronsted basic group include amine-based basic groups such as a substituent having an amine structure, a substituent having an imine structure, a substituent having an amide structure and a substituent having an imide structure.

Accordingly, as such a polyvinyl acetal resin, polyvinyl acetal resins are preferable containing as a structural unit at least one selected from the group consisting of a structural unit having an amine structure, a structural unit having an imine structure, a structural unit having an amide structure and a structural unit having an imide structure. The polyvinyl acetal resin more preferably has at least one structural unit selected from the group consisting of a structural unit having an amine structure, a structural unit having an imine structure and a structural unit having an amide structure.

In the polyvinyl acetal resin, the total content of the structural unit having an amine structure, the structural unit having an imine structure, the structural unit having an amide structure and the structural unit having an imide structure is preferably 0.1 mol % to 30 mol %, and more preferably 1 mol % to 10 mol % from the viewpoint of cell adhesion immediately after seeding.

In the polyvinyl acetal resin, the total content of the structural unit having an amine structure, the structural unit having an imine structure and the structural unit having an amide structure is preferably 0.1 mol % to 30 mot, and more preferably 1 mol % to 10 mol % from the viewpoint of cell adhesion immediately after seeding.

In the present invention, the imine structure refers to a structure having a C=N bond. The polyvinyl acetal resin preferably has an imine structure on the side chain. In addition, the imine structure may be directly bonded to a carbon atom constituting the main chain of the polyvinyl acetal resin, or may be bonded to the main chain via a linking group such as an alkylene group. Note that having the imine structure on the side chain includes having the imine structure on the graft chain of the polyvinyl acetal resin. Examples of the structural unit having an imine structure include a structural unit represented by the following formula (1).

[Chemical 1]

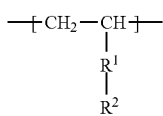

(1)

In the formula (1), $R^1$ represents a single bond or an alkylene group, and $R^2$ represents a group having an imine structure.

In the formula (1), when $R^1$ is an alkylene group, the preferred lower limit of the number of carbon atoms in the alkylene group is 1, and the preferred upper limit is 12. When the number of carbon atoms in the alkylene group exceeds 12, optimum strength may not be obtained. When $R^1$ is an alkylene group, the more preferred upper limit of the number of carbon atoms in the alkylene group is 5.

In the formula (1), when $R^1$ is an alkylene group, examples of the alkylene group includes linear alkylene groups such as a methylene group, ethylene group, trimethylene group, tetramethylene group, pentamethylene group, hexamethylene group, octamethylene group and decamethylene group, branched alkylene groups such as a methyl methylene group, methylethylene group, 1-methylpentylene group and 1,4-dimethylbutylene group, and cyclic alkylene groups such as a cyclopropylene group, cyclobutylene group and cyclohexylene group. Among them, a linear alkyl group such as a methylene group, ethylene group, trimethylene group and tetramethylene group is preferable, and a methylene group and ethylene group are more preferable.

The $R^2$ includes a functional group represented by the following formula (2).

[Chemical 2]

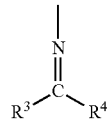

(2)

In the formula (2), $R^3$ represents a hydrogen atom or a hydrocarbon group having 1 to 18 carbon atoms, and R represents a hydrocarbon group having 1 to 18 carbon atoms.

The hydrocarbon group includes a saturated hydrocarbon group, an unsaturated hydrocarbon group and an aromatic hydrocarbon group. The hydrocarbon group may be one composed of only any one of a saturated hydrocarbon group, an unsaturated hydrocarbon group and an aromatic hydrocarbon group, or one in which two or more of them are used.

Examples of the saturated hydrocarbon group include methyl, ethyl, n-propyl, isopropyl, n-butyl, iso-butyl, sec-butyl, tert-butyl, pentyl, hexyl, heptyl, 2-ethylhexyl, octyl, nonyl, decyl, undecyl, dodecyl, tridecyl, tetradecyl, pentadecyl and octadecyl groups. Among them, a methyl group, ethyl group, n-propyl group and n-butyl group are preferable.

Examples of the aromatic hydrocarbon group include a phenyl group, toluyl group, xylyl group, t-butylphenyl group and benzyl group.

In the modified polyvinyl acetal resin, it is preferable that in the structural unit having an imine structure, $R^1$ is a single bond, $R^3$ is a hydrogen atom, a methyl group or an ethyl group, and $R^4$ is a methyl group, an ethyl group or a propyl group.

In the polyvinyl acetal resin, the preferred lower limit of the content of the structural unit having an imine structure is 0.1 mol %, and the preferred upper limit is 20.0 mol %. When the content of the structural unit having an imine structure is 0.1 mol % or more, the viscosity stability over time becomes better. When the content of the structural unit having an imine structure is 20.0 mol % or less, acetalization can be sufficiently advanced. The more preferred lower limit of the content of the structural unit having an imine structure is 1.0 mol %, and the more preferred upper limit is 15.0 mol %.

The content of the structural unit having an imine structure can be measured by $^1$H-NMR measurement.

In the polyvinyl acetal resin, the ratio between the content of the structural unit having an imine structure and the degree of acetalization described below (the content of the structural unit having an imine structure/degree of acetalization) is preferably 0.001 to 0.5. Within the above range, high strength and excellent adhesiveness can be achieved at the same time, and the durability after adhesion can be improved.

The polyvinyl acetal resin preferably has a structural unit having an imino group (—NH) (a structural unit having an imino structure).

The polyvinyl acetal resin preferably has the imino group on the side chain. In addition, the imino group may be directly bonded to a carbon atom constituting the main chain of the polyvinyl ace-al resin, or may be bonded to the main chain via a linking group such as an alkylene group.

The modified polyvinyl acetal resin preferably has a structural unit having an amine structure or a structural unit having an amide structure.

The modified polyvinyl acetal resin preferably has the amine structure or the amide structure on the side chain. In addition, the amine structure or the amide structure may be directly bonded to a carbon atom constituting the main chain of the modified polyvinyl acetal resin, or may be bonded to the main chain via a linking group such as an alkylene group. Furthermore, the amine structure may be a primary amine, a secondary amine, a tertiary amine or a quaternary amine. Among them, a primary amine is preferable from the viewpoint of enhancing the fixation of cells.

Note that having the amine structure or the amide structure on the side chain means having the amine structure or the amide structure on the graft chain of the modified polyvinyl acetal resin.

In particular, the amine structure is preferably —NH$_2$. In the present invention, the amide structure refers to a structure having —C(=O)—NH—. In particular, the structural unit having the amine structure preferably is a structure represented by the following formula (3). In addition, the structural unit having the amide structure preferably has a structure represented by the following formula (4).

[Chemical 3]

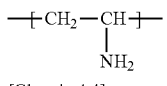
(3)

[Chemical 4]

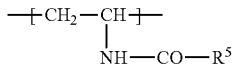
(4)

In the formula (4), R$^5$ represents a hydrogen atom or a hydrocarbon group having 1 to 10 carbon atoms. The hydrocarbon group includes an alkyl group, an alkenyl group, a cycloalkyl group and a cycloalkenyl group.

The preferred lower limit of the content of the structural unit having an amine structure or an amide structure is 0.1 mol %, and the preferred upper limit is 20 mol %. When the content of the structural unit having an amine structure or an amide structure is 0.1 mol % or more, additional properties can be made sufficient. When the content is 20 mol % or less, the solubility is not so excessively increased that the modified polyvinyl acetal resin powder can be easily taken out by precipitation method. The more preferred lower limit of the content is 0.5 mol %, and the more preferred upper limit is 10 mol %. The content of the structural unit having an amine structure or an amide structure can be measured by $^1$H-NMR measurement. In addition, the preferred lower limit of the total content of the structural unit having an amine structure or an amide structure and the structural unit having an imine structure is 0.1 mol %, and the preferable upper limit is 20 mol %. The more preferred lower limit of the content is 0.5 mol %, and the more preferred upper limit is 10 mol %.

In the polyvinyl acetal resin, the ratio between the content of the structural unit having an imine structure and that of the structural unit having an amine structure or an amide structure (the structural unit having an imine structure/the structural unit having an amino group or an amide structure) is preferably 0.5/99.5 to 99.5/0.5. When the ratio is 0.5/99.5 or more, the viscosity stability over time can be sufficient, whereas when the above ratio is 99.5/0.5 or less, the crosslinking performance can be sufficiently exhibited from the viewpoint of improving the fixation of cells. The more preferred lower limit of the ratio is 5/95, and the more preferred upper limit is 90/10.

The Bronsted acidic group is a generic term for a functional group that can deliver a hydrogen ion H$^+$ to another substance.

The Bronsted acidic group includes a carboxyl group, a sulfonic acid group, a maleic acid group, a sulfinic acid group, a sulfenic acid group, a phosphoric acid group, a phosphonic acid group, and salts thereof. Among them, a carboxyl group is preferable as the Bronsted acidic group.

The method for modifying the polyvinyl acetal resin with the Bronsted acidic group is not particularly limited, but includes a method for copolymerizing the polyvinyl alcohol with the itaconic acid or (meth)acrylic acid and a method for introducing a Bronsted acidic group into the side chain of the polyvinyl alcohol.

The degree of acetalization of the polyvinyl acetal resin is not particularly limited, but the lower limit is preferably 60 mol %, and the upper limit is preferably 90 mol %. When the degree of acetalization is 60 mol % or more, the fixation of cells is excellent, and thus cell proliferation can be performed with high efficiency. When the degree of acetalization is 90 mol % or less, the solubility in solvent can be better. The lower limit is more preferably 65 mol %, and the upper limit is more preferably 85 mol %. The degree of acetal of the polyvinyl acetal resin can be measured by $^1$H-NMR measurement.

The amount of the acetyl group in the polyvinyl acetal resin is not particularly limited, but the lower limit is preferably 0.0001 mol % and the upper limit is preferably 5 mol %.

Examples of the method for producing the polyvinyl acetal resin include a method for acetalizing using a conventionally known method a polyvinyl alcohol obtained by saponifying polyvinyl acetate obtained by copolymerizing the monomer having an imine structure with vinyl acetate. In addition, a method may also be used for introducing an imine structure by acetalizing using a conventionally known method a polyvinyl alcohol having a structural unit having an amino group or an amide structure. A method may also be used for acetalizing using a conventionally known method a modified polyvinyl alcohol having an imine structure obtained by post-modifying a polyvinyl alcohol having a structural unit having an amino group or an amide structure. Furthermore, an imine structure may be introduced by post-modifying an unmodified polyvinyl acetal resin. In other words, the modified polyvinyl acetal resin may be an acetalized product of a polyvinyl alcohol having a structural unit having an amino group or an amide structure. Among them, a method is preferable for producing a modified polyvinyl acetal resin having an imine structure by acetalizing a polyvinyl alcohol having a structural unit having an amino group or an amide structure. In particular, when such a method is used, an imine structure can be obtained by adding excessive amounts of aldehyde and acid catalyst for use in acetalization.

In the method for excessively adding aldehyde, it is preferable to add 70 to 150 parts by weight aldehyde to 100 parts by weight a polyvinyl alcohol having a structural unit having an amino group or an amide structure. Particularly, as the aldehyde, acetaldehyde, propionaldehyde, n-butyraldehyde, isobutyraldehyde, n-valeraldehyde and phenylaldehyde are preferable.

In the method for excessively adding an acid catalyst, it is preferable to add the acid catalyst in an amount of 0.5% by weight or more with respect to the whole weight. In addition, it is preferable to add 5.0 to 70.0 parts by weight acid catalyst to 100 parts by weight a polyvinyl alcohol having a structural unit having an amino group or an amide structure. Particularly, as the acid catalyst, hydrochloric acid, nitric acid, sulfuric acid and para-toluenesulfonic acid are preferable. In the case where such a method is used, examples of the method for confirming a structural unit having an amino group or an amide structure, or a structural unit having an imine structure include a confirming method by $^1$H-NMR.

The acetalization can be performed using a known method, and is preferably performed in an aqueous solvent, a mixed solvent of water and an organic solvent having compatibility with water, or an organic solvent. As the organic solvent compatible with water, for example, an alcohol-based organic solvent can be used. Examples of the organic solvent include alcohol-based organic solvents, aromatic organic solvents, aliphatic ester-based solvents, ketone-based solvents, lower paraffin-based solvents, ether-based solvents, amide-based solvents and amine-based solvents.

Examples of the alcohol-based organic solvent include methanol, ethanol, n-propanol, isopropanol, n-butanol and tert-butanol.

Examples of the aromatic organic solvent include xylene, toluene, ethylbenzene and methyl benzoate.

Examples of the aliphatic ester-based solvent include methyl acetate, ethyl acetate, butyl acetate, methyl propionate, ethyl propionate, methyl butyrate, ethyl butyrate, methyl acetoacetate and ethyl acetoacetate.

Examples of the ketone-based solvent include acetone, methyl ethyl ketone, methyl isobutyl ketone, cyclohexanone, methylcyclohexanone, benzophenone and acetophenone.

The lower paraffin-based solvents include hexane, pentane, octane, cyclohexane and decane.

The ether-based solvents include diethyl ether, tetrahydrofuran, ethylene glycol dimethyl ether, ethylene glycol diethyl ether and propylene glycol diethyl ether.

The amide-based solvents include N,N-dimethylformamide, N, N-dimethylacetamide, N-methylpyrrolidone and acetanilide.

The amine-based solvents include ammonia, trimethylamine, triethylamine, n-butylamine, di-n-butylamine, tri-n-butylamine, aniline, N-methylaniline, N,N-dimethylaniline and pyridine.

These can be used alone or as a mixture of two or more solvents. Among them, ethanol, n-propanol, isopropanol and tetrahydrofuran are particularly preferable from the viewpoints of solubility in a resin and simplicity during purification.

The acetalization is preferably performed in the presence of an acid catalyst. The acid catalyst is not particularly limited, but includes mineral acids such as sulfuric acid, hydrochloric acid, nitric acid and phosphoric acid, carboxylic acids such as formic acid, acetic acid and propionic acid, and sulfonic acids such as methanesulfonic acid, ethanesulfonic acid, benzenesulfonic acid and para-toluenesulfonic acid. These acid catalysts may be used alone or in combination of two or more compounds. Among them, hydrochloric acid, nitric acid and sulfuric acid are preferable, and hydrochloric acid is particularly preferable.

(Other Details of Scaffolding Material for Cell Culture)

The scaffolding material for cell culture according to the present invention is used for culturing cells. The scaffolding material for cell culture according to the present invention is used as a scaffold for cells when the cells are cultured. In the scaffolding material for cell culture according to the present invention, it is particularly preferable that a cell mass be seeded. However, in the scaffolding material for cell culture according to the present invention, a cell mass may not be seeded.

The cells include animal cells such as human, mouse, rat, pig, bovine and monkey cells. In addition, the cells include somatic cells, such as stem cells, progenitor cells and mature cells. The somatic cell may also be cancer cells.

The mature cells include nerve cells, cardiomyocytes, retinal cells and hepatocytes.

The stem cells include mesenchymal stem cells (MSCs), iPS cells, ES cells, Muse cells, embryonal cancer cells, embryonic germ stem cells and mGS cells.

The scaffolding material for cell culture according to the present invention is preferably in the form of a film.

[Cell Culture Method]

According to the scaffolding material for cell culture, various cells can be cultured. The cells include the above described cells. This is because the scaffolding material for cell culture according to the present invention is hardly swelled with the water in a culture medium, and thus can maintain so suitable hydrophilicity and strength that the fixation rate of cells after seeding is improved.

The cell culture method preferably includes a step of seeding a cell mass on the scaffolding material for cell culture. The cell mass can be obtained by adding a cell detaching agent to a confluent culture container and uniformly performing crushing by pipetting. The cell detaching agent is not particularly limited, but is preferably an ethylenediamine/phosphate buffer solution. The size of the cell mass is preferably 50 μm to 200 μm.

In cell culture, the scaffolding material for cell culture can be used not only for planar culture (two-dimensional culture method) but also for culturing cells on a base material in a state closer to an in-vivo state, such as a porous membrane or a hydrogel (three-dimensional culture method). This is because cells can be efficiently proliferated by using the scaffolding material for cell culture in a bioreactor or the like.

The scaffolding material for cell culture is preferably used in a two-dimensional culture method because it has suitable hydrophilicity and strength.

The container for planar culture (two-dimensional culture method) is not particularly limited for shape and size, but includes a test plate for cell culture having one or more wells (holes) and a flask for cell culture. The number of wells in the microplate is not limited, but includes, for example, 2, 4, 6, 12, 24, 48, 96 and 384. The shape of the well is not particularly limited, but includes, for example, a perfect circle, ellipse, triangle, square, rectangle, and pentagon. The shape of the bottom surface of the well is not particularly limited, but includes a flat bottom, a round bottom and irregularities.

The material of the test plate for cell culture having one or more wells (holes) or the material of the flask for cell culture are not particularly limited, but includes a polymer resin, metal and inorganic material. The polymer resin includes polystyrene, polyethylene, polypropylene, polycarbonate, polyester, polyisoprene, cycloolefin polymer, polyimide, polyamide, polyamideimide, (meth)acrylic resin, epoxy resin and silicone. The metal includes stainless steel, copper, iron, nickel, aluminum, titanium, gold, silver and platinum. The inorganic material includes silicon oxide (glass), aluminum oxide, titanium oxide, zirconium oxide, iron oxide and silicon nitride.

In addition to the above, the scaffolding material for cell culture can be used in a suspension culture method in which cells are freely suspended and grown in a medium.

Other Embodiments

In addition to the scaffolding material for cell culture, the present invention provides an invention using the scaffolding material for cell culture as another embodiment.

For example, in the present invention, a carrier (medium) for cell culture containing the scaffolding material for cell culture and a polysaccharide is provided. Various polysaccharides can be used as the polysaccharide without any particular limitation. Among them, water-soluble polysaccharides are preferable.

In addition, in the present invention, a container for cell culture provided with a resin film on at least a part of a cell culture region is provided, wherein the scaffolding material for cell culture is used as the resin film. The container is not particularly limited as long as it has a resin film on at least a part of the cell culture region, but various containers can be used. As the container, the container for planar culture, a bioreactor or the like can be used.

In addition, the present invention provides a fiber for cell culture containing the scaffolding material for cell culture. In this case, it is preferable that the scaffolding material for cell culture be applied on the fiber. In addition, the scaffolding material for cell culture may be in a form impregnated or kneaded in the fiber. The fiber for cell culture is suitable for a three-dimensional culture method for cells that are difficult to adhere to a planar structure such as a flask, but easily adhere to a three-dimensional structure such as a fibril-like structure.

The scaffolding material for cell culture may be crosslinked. This is because crosslinking can suppress water swelling and suitably increase the strength. Using a crosslinking agent can provide the crosslinked scaffolding material for cell culture.

The crosslinking agent is not particularly limited, but includes polyalcohol, polycarboxylic acid, hydroxycarboxylic acid, metal soap and polysaccharides.

The polyalcohol is not particularly limited, but includes ethylene glycol, propylene glycol, butanediol, pentanediol, hexanediol, heptanediol, octanediol, nonanediol, decanediol, dodecanediol, undecanediol, diethylene glycol, triethylene glycol, tetraethylene glycol, polyethylene glycol, catechol, pyrogallol, diboronic acid, methylenediboronic acid, ethylenediboronic acid, propylene diboronic acid, phenylenediboronic acid, biphenyldiboronic acid and bisphenol derivatives.

The polycarboxylic acid is not particularly limited, but includes oxalic acid, malonic acid, succinic acid, glutaric acid, adipic acid, pimelic acid, suberic acid, azelaic acid, sebacic acid, phthalic acid and poly(meth)acrylic acid.

The hydroxycarboxylic acid is not particularly limited, but includes glycolic acid, lactic acid, tartronic acid, glyceric acid, hydroxybutyric acid, malic acid, tartaric acid, cytomaric acid, citric acid, isocitric acid, leucic acid, mevalonic acid, pantoic acid, ricinoleic acid, ricineraidic acid, cerebronic acid, quinic acid, shikimic acid, hydroxybenzoic acid, salicylic acid, creosotic acid, vanillic acid, syringic acid, pyrocatechuic acid, resorcylic acid, protocatechuic acid, gentisic acid, orsellinic acid, gallic acid, mandelic acid, benzylic acid, atrolactic acid, melilotic acid, phloretic acid, coumaric acid, umbellic acid, caffeic acid, ferulic acid, sinapinic acid and hydroxystearic acid.

The metal soap is not particularly limited, but includes salts of fatty acids such as stearic acid, lauric acid, ricinoleic acid and octylic acid with metals such as lithium, sodium, magnesium, calcium, barium, zinc and aluminum.

The polysaccharides are not particularly limited, but include pectin, guar gum, xanthan gum, tamarind gum, carrageenan, propylene glycol, carboxymethylcellulose, amylose, amylopectin, glycogen, cellulose, chitin, agarose, carrageenan, heparin, hyaluronic acid, xyloglucan and glucomannanic acid.

EXAMPLES

Hereinafter, a description is made of the present invention with reference to Examples and Comparative Examples, but the present invention is not limited to the following Examples. The content of the structural unit, for example, structural unit having an amine structure (mol %), content of the structural unit having an imine structure (mol %), content of the structural unit having an amide structure (mol %), degree of acetalization (mol %), amount of acetyl group (mol %), amount of hydroxyl group (mol %) and amount of (meth)acrylic ester (mol %) in an obtained synthetic resin, modified polyvinyl acetal resin were measured by dissolving the synthetic resin in DMSO-d6 (dimethyl sulfoxide) and using $^1$H-NMR (nuclear magnetic resonance spectrum).

Example 1

Preparation of Polyvinyl Butyral

A reactor equipped with a stirrer was charged with 2700 mL of ion-exchanged water, 300 g of polyvinyl alcohol having an average degree of polymerization of 250 and a degree of saponification of 99 mol %, followed by dissolution by heating with stirring to prepare a solution. Next, to the solution, 35% by weight hydrochloric acid as a catalyst was added such that the concentration of hydrochloric acid became 0.2% by weight, and after the temperature was adjusted to 15° C., 22 g of n-butyraldehyde (n-BA) was added while being stirred. Thereafter, when 148 g of n-butyraldehyde (n-BA) was added, polyvinyl butyral was precipitated in the form of white particles. Fifteen minutes after the precipitation, 35% by weight hydrochloric acid was added such that the concentration of hydrochloric acid became 1.8% by weight, followed by heating to 50° C. for aging at 50° C. for 2 hours. Next, the solution was cooled and neutralized, and then the polyvinyl butyral was washed with water and dried.

The obtained polyvinyl butyral had an average degree of polymerization of 250, an amount of hydroxyl group of 28 mol %, an amount of acetyl group of 1 mol % and a degree of acetalization of 71 mol %.

Preparation of Container for Cell Culture

By dissolving 1 g of the obtained polyvinyl butyral in 19 g of butanol, a solution of polyvinyl butyral was obtained. By discharging 150 μL of the obtained solution of polyvinyl butyral onto a φ22 mm cover glass (manufactured by Matsunami Glass Ind., Ltd., 22 round No. 1 was used after dust was removed with air duster) and spinning it at 2,000 rpm for 20 seconds using a spin coater, a smooth resin film was obtained. By placing the obtained resin film on a φ22 mm polystyrene dish together with the cover glass, a container for cell culture was obtained.

(Surface Free Energy)

The surface free energy of the resin film was measured using a contact angle meter (manufactured by Kyowa Interface Science, Inc., DMo-701). A contact angle of pure water was obtained by dropping 1 μL of pure water onto the resin film, and then photographing the droplet image after 30 seconds. In addition, a contact angle of diiodomethane was obtained by dropping 1 μL of diiodomethane onto the resin film, and then photographing the droplet image after 30 seconds. From the obtained contact angles, the surface free energy γ, dispersion component $γ^d$ and dipole component $γ^p$ were derived using the Kaelble-Uy theoretical formula.

Using the obtained container for cell culture, tests were conducted under the following conditions.

(Method for Cell Culture Test (iPS Cells))

To the obtained container for cell culture, 1 mL of phosphate buffered saline was added, and the mixture was allowed to stand for 1 hour in an incubator at 37° C. After removing the phosphate buffered saline in the dish, $1.5 \times 10^4$ h-iPS cells 253G1 were seeded for performing culture in the presence of 1 mL of medium TeSR E8 (manufactured by STEM CELL) and 10 μM of ROCK-Inhibitor (Y27632) in an incubator at 37° C. under a $CO_2$ concentration of 5%. Every 24 hours, the medium was exchanged by removing 750 μL of medium, and adding 250 μL of new TeSR E8 such that the ROCK-Inhibitor (Y27632) was adjusted to be at 10 μM.

(Method for Cell Mass Culture Test (iPS Cells))

To the obtained container for cell culture, 1 mL of phosphate buffered saline was added, and the mixture was allowed to stand for 1 hour in an incubator at 37° C. Thereafter, the phosphate buffered saline in the culture container was removed. A confluent colony of h-iPS cells 252G1 was added to a 35 mm dish, and then 1 mL of 0.5 mM ethylenediamine/phosphate buffer solution was added, followed by standing at room temperature for 2 minutes. Thereafter, the ethylenediamine/phosphate buffer solution was removed, $1.0 \times 10^5$ cell mass crushed to 50 to 200 μm by pipetting with 1 mL of TeSR E8 medium was seeded in the culture container for performing culture in the presence of 1 mL of medium TeSR E8 (manufactured by STEM CELL) and 10 μM of ROCK-Inhibitor (Y27632) in an incubator at 37° C. under a $CO_2$ concentration of 5%. Every 24 hours, the medium was exchanged by removing 750 μL of the medium and adding 250 μL of new TeSR E8.

(Method for Evaluating iPS Cell Culture)
(1) Initial Adhesion (iPS Cells)

In the cell culture test for iPS cells, a cell image 24 hours after the cell seeding was obtained using a phase-contrast microscope (manufactured by Olympus Corporation, IX73) at a magnification of 10×10. At that time, an image of a visual field showing the most average form of adhesion in the culture container was obtained. The obtained images were compared with Samples 1 to 10 in FIG. 4 to evaluate the initial adhesion in consideration of the number of adherent cells and the morphology of adherent cells. In FIG. 4, it is shown that the number of cells increases from Samples 1 to 8 in this order. In addition, it is shown that the pseudopodia of the cells elongate and the cells are in a better adhesion state, from Samples 8 to 10 in this order. The obtained results are summarized in FIGS. 5 and 6.

(2) Cell Proliferation (iPS Cells)

In the cell culture test for iPS cells, a cell image 5 days after the cell seeding was obtained using a phase-contrast microscope (manufactured by Olympus Corporation, IX73) at a magnification of 10×4. At that time, an image of a visual field showing the most average form of adhesion in the culture container was obtained. The cell proliferation was evaluated by comparing the obtained image with Samples 1 to 10 in FIG. 7. In FIG. 7, a higher evaluation was obtained as the colony grew due to cell proliferation. When the colony grows too much in the lateral direction (the vertical and horizontal direction in the view), it starts to pile up in the vertical direction (the direction toward the front side of the view), so that light transmittance tends to decrease. The obtained results are summarized in FIGS. 8 and 9.

(3) Adhesion Maintenance (iPS Cells)

In the cell mass culture test for iPS cells, the time during which the cell mass could maintain adhesion was evaluated according to the following criteria.

0: All cells were detached in less than 30 minutes after medium exchange.
1: Adhesion was maintained for 30 minutes or more after medium exchange, but all cells were detached in less than 1 hour.
2: Adhesion was maintained for 1 hour or more after medium exchange, but all cells detached in less than 24 hours.
3: Adhesion was maintained for 24 hours or more after medium exchange.

The obtained cell mass was confirmed to maintain undifferentiation by alkaline phosphatase (ALP) staining test.
(Method for Cell Culture Test (Hepatocytes))

To the obtained container for cell culture, 1 mL of phosphate buffered saline was added, and the mixture was allowed to stand for 1 hour in an incubator at 37° C. After removing the phosphate buffered saline in the dish, $3 \times 10^4$ cells of human fresh hepatocytes derived from a chimeric mouse (PXB-cells manufactured by PhoenixBio Co., Ltd.) were seeded. Next, 1 mL of medium RM-101 (manufactured by Toyo Gosei Co., Ltd.) was added, followed by culture in an incubator at 37° C. with a $CO_2$ concentration of 5%.
(Method for Evaluating Hepatocyte Culture)
(4) Initial Adhesion (Fixation after Seeding) (Hepatocytes)

In the cell culture test for hepatocytes, cells were detached using trypsin 24 hours after seeding of the cells. The number of cells was measured using an auto cell counter (Auto Cell Counter EVE, manufactured by NanoEnteck Inc.).

<Evaluation Criteria for Initial Adhesion (Hepatocytes)>
  ○○○: The number of cells is $2.5 \times 10^4$ cells or more
  ○○: The number of cells is $1.5 \times 10^4$ cells or more and less than $2.5 \times 10^4$ cells ○: The number of cells is $1.0 \times 10^4$ cells or more and less than $1.5 \times 10^4$ cells x: The number of cells is less than $1.0 \times 10^4$ cells (5) Cell Proliferation (Hepatocytes)

In the cell culture test for hepatocytes, cells were detached using trypsin 3 days after seeding of the cells. The number of cells was measured using an auto cell counter (Auto Cell Counter EVE, manufactured by NanoEnteck Inc.).

<Evaluation Criteria for Cell Proliferation (Hepatocytes)>

○○○: The number of cells is $2.0 \times 10^5$ cells or more

○○: The number of cells is $1.0 \times 10^5$ cells or more and less than $2.0 \times 10^5$ cells ○: The number of cells is $5.0 \times 10^4$ cells or more and less than $1.0 \times 10^5$ cells x: The number of cells is less than $5.0 \times 10^4$ cells Example 2

The test was performed in the same manner as in Example 1 except that polyvinyl alcohol having an average degree of polymerization of 850 and a degree of saponification of 99 mol % was used.

Example 3

The test was performed in the same manner as in Example 1 except that polyvinyl alcohol having an average degree of polymerization of 1,700 and a degree of saponification of 99 mol % was used.

Example 4

The test was performed in the same manner as in Example 1 except that polyvinyl alcohol having an average degree of polymerization of 2,400 and a degree of saponification of 99 mol % was used, and that acetaldehyde was used instead of n-butyraldehyde (n-BA).

Example 5

The test was performed in the same manner as in Example 1 except that polyvinyl alcohol having an average degree of polymerization of 850, a degree of saponification of 98 mol %, and a degree of ethylene modification of 4 mol % was used.

Example 6

The test was performed in the same manner as in Example 1 except that polyvinyl alcohol having an average degree of polymerization of 250 and a degree of saponification of 99 mol %, and containing 2 mol % structural unit having an amino group represented by the formula (3) was used.

Example 7

The test was performed in the same manner as in Example 1 except that polyvinyl alcohol having an average degree of polymerization of 1,600 and a degree of saponification of 99 mol %, and containing 2 mol % structural unit having an amino group represented by the formula (3) was used.

Example 8

In 500 parts by weight tetrahydrofuran, 100 parts by weight polyvinyl acetal having a degree of polymerization of about 250 obtained in Example 1 and 1 part by weight N-vinylpyrrolidone were dissolved to prepare a graft copolymer resin solution. In the prepared resin solution, 0.05 parts by weight Irgacure184 (manufactured by BASF) was dissolved, and the resultant mixture was applied onto a PET film. The coated product was irradiated with light having a wavelength of 365 nm at an integrated light amount of 2000 mJ/cm$^2$ using a UV conveyor device "ECS301G1" manufactured by Eye Graphics Co., Ltd. at 25° C. to prepare a composite resin solution. The prepared composite resin solution was vacuum-dried at 80° C. for 3 hours to prepare a composite resin. The prepared composite resin was measured for weight average molecular weight in terms of polystyrene by GPC method using "2690 Separations Model" manufactured by Waters Corporation as a column. The weight average molecular weight was about 40,000. The prepared composite resin was adjusted to a 3% by weight butanol solution, and the test was conducted in the same manner as in Example 1.

Example 9

The test was performed in the same manner as in Example 8 except that 10 parts by weight N-vinylpyrrolidone was added to 100 parts by weight polyvinyl acetal. The weight average molecular weight of the obtained resin was about 60,000.

Example 10

The test was performed in the same manner as in Example 8 except that 30 parts by weight N-vinylpyrrolidone was added to 100 parts by weight polyvinyl acetal. The weight average molecular weight of the obtained resin was about 50,000.

Example 11

The test was performed in the same manner as in Example 8 except that 5 parts by weight tetrahydrofurfuryl acrylate was added to 100 parts by weight polyvinyl acetal. The weight average molecular weight of the obtained resin was about 60,000.

Example 12

The test was performed in the same manner as in Example 8 except that 5 parts by weight methoxyethyl acrylate was added to 100 parts by weight polyvinyl acetal. The weight average molecular weight of the obtained resin was about 70,000.

Example 13

The test was performed in the same manner as in Example 8 except that 5 parts by weight butyl methacrylate was added to 100 parts by weight polyvinyl acetal. The weight average molecular weight of the obtained resin was about 60,000.

Example 14

In 300 parts by weight tetrahydrofuran, 75 parts by weight N-isopropylacrylamide and 25 parts by weight butyl methacrylate were dissolved to prepare an acrylic monomer solution. In the prepared acrylic monomer solution, 2 parts by weight Irgacure184 (manufactured by BASF) was dissolved, and the resultant mixture was applied onto a PET film. The coated product was irradiated with light having a wavelength of 365 nm at an integrated light amount of 2,000 mJ/cm² using a UV conveyor device "ECS301G1" manufactured by Eye Graphics Co., Ltd. at 25° C. to prepare an acrylic resin solution. The prepared acrylic resin solution was vacuum-dried at 80° C. for 3 hours to prepare an acrylic resin. The prepared acrylic resin was adjusted to a 3% by weight butanol solution, and the test was conducted in the same manner as in Example 1. The weight average molecular weight of the obtained acrylic resin was about 100,000.

Example 15

An acrylic resin was obtained in the same manner as in Example 14 except that 90 parts by weight methoxyethyl acrylate and 10 parts by weight butyl methacrylate were used, instead of 75 parts by weight N-isopropylacrylamide and 25 parts by weight butyl methacrylate. The prepared acrylic resin was adjusted to a 3% by weight butanol solution, and the test was conducted in the same manner as in Example 1. The weight average molecular weight of the obtained acrylic resin was about 80,000.

Example 16

An acrylic resin was obtained in the same manner as in Example 14 except that 75 parts by weight methoxyethyl acrylate and 25 parts by weight butyl methacrylate were used, instead of 75 parts by weight N-isopropylacrylamide and 25 parts by weight butyl methacrylate. The prepared acrylic resin was adjusted to a 3% by weight butanol solution, and the test was conducted in the same manner as in Example 1. The weight average molecular weight of the obtained resin was about 90,000.

Example 17

An acrylic resin was obtained in the same manner as in Example 14 except that 2 parts by weight butyl methacrylate and 98 parts by weight ethyl acrylate were used, instead of 75 parts by weight N-isopropylacrylamide and 25 parts by weight butyl methacrylate. The prepared acrylic resin was adjusted to a 3% by weight butanol solution, and the test was conducted in the same manner as in Example 1. The weight average molecular weight of the obtained acrylic resin was about 80,000.

Comparative Example 1

The test was performed in the same manner as in Example 1 using only a polystyrene dish without using the scaffolding material.

Comparative Example 2

The test was performed in the same manner as in Example 1 except that the amount of the second addition of n-butyraldehyde (n-BA) was changed from 148 g to 89 g.

Comparative Example 3

The test was performed in the same manner as in Example 1 except that polyvinyl alcohol having an average degree of polymerization of 1000 and a degree of saponification of 98 mol % was used as the synthetic resin.

Comparative Example 4

A polyacrylamide resin was obtained by mixing 100 parts by weight N-isopropylacrylamide, 75 parts by weight ethyl acetate and 0.5 parts by weight azobisisobutyronitrile, followed by polymerization at 65° C. for 8 hours under a nitrogen atmosphere. The prepared resin was measured for weight average molecular weight in terms of polystyrene by GPC method using "2690 Separations Model" manufactured by Waters Corporation as a column. The weight average molecular weight was about 90,000 (the degree of polymerization was about 800). Other operations in the test were performed in the same manner as in Example 1.

Comparative Example 5

The test was performed in the same manner as in Comparative Example 4 except that 100 parts by weight ethyl acrylate was used instead of 100 parts by weight N-isopropylacrylamide.

Comparative Example 6

The test was performed in the same manner as in Comparative Example 4 except that 100 parts by weight butyl methacrylate was used instead of 100 parts by weight N-isopropylacrylamide. The weight average molecular weight of the obtained resin was about 90,000.

Comparative Example 7

The test was performed in the same manner as in Example 8 except that 70 parts by weight N-vinylpyrrolidone was added to 30 parts by weight polyvinyl acetal. The weight average molecular weight of the obtained resin was about 90,000.

The obtained results are summarized in Tables 1 to 4. FIGS. 5 and 6 show phase contrast micrographs of the cells 24 hours after seeding. FIGS. 8 and 9 show phase contrast micrographs of the cells 5 days after seeding. No differentiated cells were observed in any of the Examples and Comparative Examples.

TABLE 1

| | | | Example 1 | Example 2 | Example 3 | Example 4 | Example 5 |
|---|---|---|---|---|---|---|---|
| Synthetic resin | Polyvinyl acetal resin | Degree of acetalization (mol %) | 71 | 68 | 65 | 66 | 64 |
| | | Amount of acetyl group (mol %) | 1 | 1 | 1 | 1 | 2 |
| | | Amount of hydroxyl group (mol %) | 28 | 31 | 34 | 33 | 30 |
| | | Content of structural unit having amine structure (1) (mol %) | — | — | — | — | — |
| | | Content of structural unit having imine structure (2) (mol %) | — | — | — | — | — |
| | | Content of structural unit having amide structure (3) (mol %) | — | — | — | — | — |

TABLE 1-continued

|  |  |  | Example 1 | Example 2 | Example 3 | Example 4 | Example 5 |
| --- | --- | --- | --- | --- | --- | --- | --- |
|  |  | Total content of structural unit having amine structure, structural unit having imine group and structural unit having amide structure ((1) + (2) + (3)) (mol %) | — | — | — | — | — |
|  |  | Average degree of polymerization | 250 | 850 | 1700 | 2400 | 850 |
|  | Surface free energy | $\gamma^d$ (mJ/m$^2$) | 32.5 | 32.6 | 33.5 | 31.3 | 34.2 |
|  |  | $\gamma^p$ (mJ/m$^2$) | 3.5 | 3.7 | 3.5 | 4.6 | 3.3 |
| Evaluation for culture | Initial adhesion (iPS cell) |  | 5 | 5 | 6 | 6 | 6 |
|  | Cell proliferation (iPS cell) |  | 4 | 5 | 6 | 6 | 5 |
|  | Maintenance of adhesion (iPS cell) |  | 1 | 1 | 1 | 1 | 1 |
|  | Initial adhesion (hepatocyte) |  | ◯ | ◯ | ◯ | ◯ | ◯ |
|  | Cell proliferation (hepatocyte) |  | ◯ | ◯ | ◯ | ◯ | ◯ |

TABLE 2

|  |  |  | Example 6 | Example 7 | Example 8 | Example 9 | Example 10 |
| --- | --- | --- | --- | --- | --- | --- | --- |
| Synthetic resin | Polyvinyl acetal resin | Degree of acetalization (mol %) | 77 | 76 | 70 | 65 | 54 |
|  |  | Amount of acetyl group (mol %) | 1 | 1 | 1 | 1 | 1 |
|  |  | Amount of hydroxyl group (mol %) | 20 | 21 | 28 | 25 | 21 |
|  |  | Content of structural unit having amine structure (1) (mol %) | 0.3 | 0.3 | — | — | — |
|  |  | Content of structural unit having imine structure (2) (mol %) | 1.7 | 1.7 | — | — | — |
|  |  | Content of structural unit having amide structure (3) (mol %) | — | — | 1 | 9 | 24 |
|  |  | Total content of structural unit having amine structure, structural unit having imine group and structural unit having amide structure ((1) + (2) + (3)) (mol %) | 2.0 | 2.0 | 1 | 9 | 24 |
|  |  | Average degree of polymerization | 250 | 1600 | 250 | 250 | 250 |
|  | Surface free energy | $\gamma^d$ (mJ/m$^2$) | 34.2 | 34.8 | 33.0 | 35.7 | 36.2 |
|  |  | $\gamma^p$ (mJ/m$^2$) | 3.3 | 3.6 | 3.2 | 2.6 | 2.2 |
| Evaluation for culture | Initial adhesion (iPS cell) |  | 8 | 8 | 9 | 9 | 7 |
|  | Cell proliferation (iPS cell) |  | 6 | 7 | 9 | 9 | 6 |
|  | Maintenance of adhesion (iPS cell) |  | 2 | 2 | 3 | 3 | 2 |
|  | Initial adhesion (hepatocyte) |  | ◯◯ | ◯◯ | ◯◯◯ | ◯◯◯ | ◯◯ |
|  | Cell proliferation (hepatocyte) |  | ◯◯ | ◯◯ | ◯◯◯ | ◯◯◯ | ◯◯ |

TABLE 3

|  |  |  | Example 11 | Example 12 | Example 13 | Example 14 | Example 15 | Example 16 | Example 17 |
| --- | --- | --- | --- | --- | --- | --- | --- | --- | --- |
| Synthetic resin | Polyvinyl acetal resin | Degree of acetalization (mol %) | 68 | 69 | 68 | — | — | — | — |
|  |  | Amount of acetyl group (mol %) | 1 | 1 | 1 | — | — | — | — |
|  |  | Amount of hydroxyl group (mol %) | 27 | 27 | 27 | — | — | — | — |
|  |  | Content of structural unit having amine structure (1) (mol %) | — | — | — | — | — | — | — |
|  |  | Content of structural unit having imine structure (2) (mol %) | — | — | — | — | — | — | — |
|  |  | Content of structural unit having amide structure (3) (mol %) | — | — | — | — | — | — | — |
|  |  | Content of structural unit derived from tetrahydrofurfuryl acrylate (mol %) | 4 | — | — | — | — | — | — |
|  |  | Content of structural unit derived from methoxyethyl acrylate (mol %) | — | 4 | — | — | — | — | — |
|  |  | Content of structural unit derived from butyl methacrylate (mol %) | — | — | 4 | — | — | — | — |
|  |  | Total content of structural unit having amine structure, structural unit having imine group and structural unit having amide structure ((1) + (2) + (3)) (mol %) | — | — | — | — | — | — | — |
|  |  | Average degree of polymerization | 250 | 250 | 250 | — | — | — | — |

TABLE 3-continued

|  |  |  | Example 11 | Example 12 | Example 13 | Example 14 | Example 15 | Example 16 | Example 17 |
|---|---|---|---|---|---|---|---|---|---|
|  | Poly(meth) acrylic ester | Content of structural unit having amide structure (mol %) | — | — | — | 79 | — | — | — |
|  |  | Content of structural unit derived from butyl methacrylate (mol %) | — | — | — | 21 | 9 | 23 | 1 |
|  |  | Content of structural unit derived from methoxyethyl acrylate (mol %) | — | — | — | — | 91 | 77 | — |
|  |  | Content of structural unit derived from ethyl acrylate (mol %) | — | — | — | — | — | — | 99 |
|  |  | Average degree of polymerization | — | — | — | 250 | 250 | 250 | 250 |
|  | Surface free energy | $\gamma^d$ (mJ/m$^2$) | 35.1 | 34 | 34.4 | 24.8 | 38.9 | 42.9 | 42.7 |
|  |  | $\gamma^p$ (mJ/m$^2$) | 2.9 | 4.2 | 2.4 | 9.2 | 17.9 | 8.6 | 5.8 |
| Evaluation for culture | Initial adhesion (iPS cell) |  | 7 | 8 | 8 | 4 | 4 | 4 | 4 |
|  | Cell proliferation (iPS cell) |  | 8 | 8 | 8 | 3 | 3 | 3 | 3 |
|  | Maintenance of adhesion (iPS cell) |  | 2 | 2 | 2 | 1 | 1 | 1 | 1 |
|  | Initial adhesion (hepatocyte) |  | ⊚ | ⊚ | ⊚ | ○ | ○ | ○ | ○ |
|  | Cell proliferation (hepatocyte) |  | ⊚ | ⊚ | ⊚ | ○ | ○ | ○ | ○ |

TABLE 4

|  |  |  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|
| Synthetic resin | Polyvinyl acetal resin | Degree of acetalization (mol %) | — | 40 | 0 | — | — | — | 21 |
|  |  | Amount of acetyl group (mol %) | — | 3 | 2 | — | — | — | 0 |
|  |  | Amount of hydroxyl grous (mol %) | — | 57 | 98 | — | — | — | 9 |
|  |  | Content of structural unit having emine structure (1) (mol %) | — | — | — | — | — | — | — |
|  |  | Content of structural unit having imine structure (2) (mol %) | — | — | — | — | — | — | — |
|  |  | Content of structural unit having amide structure (3) (mol %) | — | — | — | — | — | — | 71 |
|  |  | Content of structural unit derived from tetrahydrofurfuryl acrylate (mol %) | — | — | — | — | — | — | — |
|  |  | Content of structural unit derived from methoxyethyl acrylate (mol %) | — | — | — | — | — | — | — |
|  |  | Content of structural unit derived from butyl methacrylate (mol %) | — | — | — | — | — | — | — |
|  |  | Total content of structural unit having amine structure, structural unit having imine group and structural unit having amide structure ((1) + (2) + (3)) (mol %) | — | — | — | — | — | — | 71 |
|  |  | Average degree of polymerization | — | 250 | 1000 | — | — | — | 250 |
|  | Poly(meth) acrylic ester | Content of structural unit having amide structure (mol %) | — | — | — | 100 | — | — | — |
|  |  | Content of structural unit derived from butyl methacrylate (mol %) | — | — | — | — | — | 100 | — |
|  |  | Content structural unit derived from methoxyethyl acrylate (mol %) | — | — | — | — | — | — | — |
|  |  | Content of structural unit derived from ethy- acrylate (mol %) | — | — | — | — | 100 | — | — |
|  |  | Average degree of polymerization | — | — | — | 800 | 600 | 550 | 250 |
|  | Surface free energy | $\gamma^d$ (mJ/m$^2$) | 45.9 | 28.9 | 26.7 | 24.0 | 23.1 | 45.7 | 24.3 |
|  |  | $\gamma^p$ (mJ/m$^2$) | 5.8 | 26.8 | 34.9 | 19.6 | 6.0 | 1.0 | 26.8 |
| Evaluation for culture | Initial adhesion (iPS cell) |  | 3 | 4 | 3 | 2 | 2 | 4 | 2 |
|  | Cell proliferation (iPS cell) |  | 1 | 2 | 1 | 1 | 1 | 1 | 1 |
|  | Maintenance of adhesion (iPS cell) |  | 0 | 0 | 0 | 0 | 0 | 0 | 0 |
|  | Initial adhesion (hepatocyte) |  | x | x | x | x | x | x | x |
|  | Cell proliferation (hepatocyte) |  | x | x | x | x | x | x | x |

What is claimed is:

1. A method for culturing a cell comprising a step of culturing a cell on a scaffolding material in a serum-free medium containing no feeder cell or adhesive protein, the scaffolding material being a resin film, and the scaffolding material having a dispersion component $\gamma^d$ of surface free energy of 28.0 mJ/m$^2$ or more and 38.0 mJ/m$^2$ or less, and a dipole component $\gamma^p$ of surface free energy of 1.0 mJ/m$^2$ or more and 10.0 mJ/m$^2$ or less, wherein the scaffolding material comprises a polyvinyl acetal resin, and wherein the polyvinyl acetal resin contains a structural unit having an amine structure, a structural unit having an imine structure, a structural unit having an amide structure, or any combination thereof.

2. The method for culturing a cell according to claim 1, comprising a step of seeding a cell mass on the scaffolding material.

3. The method for culturing a cell according to claim 1, wherein the polyvinyl acetal resin has a total content of the structural unit having an amine structure, the structural unit having an imine structure and the structural unit having an amide structure of 0.1 mol % or more and 30 mol % or less.

4. The method for culturing a cell according to claim 1, wherein the polyvinyl acetal resin is a polyvinyl butyral resin.

5. The method for culturing a cell according to claim 1, wherein a degree of acetalization of the polyvinyl acetal resin is 54 mol % or more.

6. The method for culturing a cell according to claim 1, wherein the polyvinyl acetal resin is a graft copolymer with a vinyl.

7. The method for culturing a cell according to claim 1, wherein the step of culturing a cell is a step of culturing a cell in a container comprising a cell culture region, and
 the scaffolding material is on at least a part of the cell culture region.

8. The method for culturing a cell according to claim 1, wherein the cell is a stem cell.

9. The method for culturing a cell according to claim 1, wherein the cell is a human pluripotent stem cell.

10. The method for culturing a cell according to claim 1, wherein the cell is a human embryonic stem cell (hESC) or a human induced pluripotent stem cell (hiPSC).

* * * * *